(12) United States Patent
Kankaria

(10) Patent No.: US 9,557,156 B2
(45) Date of Patent: Jan. 31, 2017

(54) OPTICAL COHERENCE TOMOGRAPHY WITH GRADED INDEX FIBER FOR BIOLOGICAL IMAGING

(71) Applicant: Avinger, Inc., Redwood City, CA (US)

(72) Inventor: Manish Kankaria, Fremont, CA (US)

(73) Assignee: Avinger, Inc., Redwood City, CA (US)

( * ) Notice: Subject to any disclaimer, the term of this patent is extended or adjusted under 35 U.S.C. 154(b) by 168 days.

(21) Appl. No.: 14/400,140

(22) PCT Filed: Mar. 15, 2013

(86) PCT No.: PCT/US2013/031951
§ 371 (c)(1),
(2) Date: Nov. 10, 2014

(87) PCT Pub. No.: WO2013/172972
PCT Pub. Date: Nov. 21, 2013

(65) Prior Publication Data
US 2015/0099984 A1    Apr. 9, 2015

Related U.S. Application Data

(60) Provisional application No. 61/646,783, filed on May 14, 2012.

(51) Int. Cl.
*A61B 6/00* (2006.01)
*G01B 9/02* (2006.01)
(Continued)

(52) U.S. Cl.
CPC ......... *G01B 9/02091* (2013.01); *A61B 5/0066* (2013.01); *A61B 5/0084* (2013.01); *G01B 9/0205* (2013.01); *G01B 9/02057* (2013.01); *G02B 6/25* (2013.01); *G02B 6/255* (2013.01); *Y10T 29/49826* (2015.01)

(58) Field of Classification Search
CPC ... A61B 5/0066; A61B 5/0084; G01B 9/0205; G01B 9/02057; G01B 9/02091; G02B 6/25; G02B 6/255; Y10T 29/49826
See application file for complete search history.

(56) References Cited

U.S. PATENT DOCUMENTS 4,178,935 A    12/1979   Gekhaman et al.
4,552,554 A    11/1985   Gould et al.
(Continued)

FOREIGN PATENT DOCUMENTS

CN    1875242 A    12/2006
CN    1947652 A    4/2007
(Continued)

OTHER PUBLICATIONS

Simpson et al.; U.S. Appl. No. 14/424,266 entitled "Re-entry stylet for catheter," filed Feb. 26, 2015.
(Continued)

*Primary Examiner* — Mark Remaly
(74) *Attorney, Agent, or Firm* — Shay Glenn LLP

(57) ABSTRACT

A system for optical coherence tomography includes a source of optical radiation, an optical fiber, and a graded index fiber attached to a distal end of the optical fiber. The optical fiber and the graded index fiber are together configured to provide a common path for optical radiation reflected from a reference interface at a distal end of the graded index fiber and from a target.

17 Claims, 17 Drawing Sheets

(51) Int. Cl.
  *A61B 5/00* (2006.01)
  *G02B 6/25* (2006.01)
  *G02B 6/255* (2006.01)

(56) References Cited

U.S. PATENT DOCUMENTS

| | | |
|---|---|---|
| 4,621,353 A | 11/1986 | Hazel et al. |
| 4,639,091 A | 1/1987 | Huignard et al. |
| 4,654,024 A | 3/1987 | Crittenden et al. |
| 4,686,982 A | 8/1987 | Nash |
| 4,771,774 A | 9/1988 | Simpson et al. |
| 4,841,977 A | 6/1989 | Griffith et al. |
| 4,926,858 A | 5/1990 | Gifford, III et al. |
| 5,000,185 A | 3/1991 | Yock |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,383,460 A | 1/1995 | Jang et al. |
| 5,383,467 A | 1/1995 | Auer et al. |
| 5,429,136 A | 7/1995 | Milo et al. |
| 5,431,673 A | 7/1995 | Summers et al. |
| 5,459,570 A | 10/1995 | Swanson et al. |
| 5,465,147 A | 11/1995 | Swanson |
| 5,507,795 A | 4/1996 | Chiang et al. |
| 5,556,405 A | 9/1996 | Lary |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,779 B1 | 9/2002 | Taylor |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,615,071 B1 | 9/2003 | Casscells, III et al. |
| 6,638,233 B2 | 10/2003 | Corvi et al. |
| 6,645,217 B1 | 11/2003 | MacKinnon et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |

(56) References Cited

U.S. PATENT DOCUMENTS

| | | |
|---|---|---|
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,706,863 B2 | 4/2010 | Imanishi et al. |
| 7,728,985 B2 | 6/2010 | Feldchtein et al. |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,644,913 B2 | 2/2014 | Simpson et al. |
| 8,696,695 B2 | 4/2014 | Patel et al. |
| 2001/0020126 A1 | 9/2001 | Swanson et al. |
| 2002/0019644 A1 | 2/2002 | Hastings et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1 | 10/2002 | Wood |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0082850 A1 | 4/2004 | Bonner et al. |
| 2004/0092915 A1 | 5/2004 | Levatter |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |

(56) References Cited

U.S. PATENT DOCUMENTS

| | | |
|---|---|---|
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0125253 A1 | 5/2010 | Olson |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0021926 A1 | 1/2011 | Spencer et al. |
| 2011/0040238 A1 | 2/2011 | Wulfman et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0301625 A1 | 12/2011 | Mauch et al. |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0289971 A1 | 11/2012 | Segermark et al. |
| 2013/0035692 A1 | 2/2013 | Sorensen et al. |
| 2013/0096589 A1 | 4/2013 | Spencer et al. |
| 2013/0123615 A1 | 5/2013 | Spencer et al. |
| 2013/0138128 A1 | 5/2013 | Patel et al. |
| 2013/0289392 A1 | 10/2013 | Patel et al. |
| 2013/0296695 A1 | 11/2013 | Spencer et al. |
| 2014/0005534 A1 | 1/2014 | He et al. |
| 2014/0213893 A1 | 7/2014 | Simpson et al. |
| 2015/0164530 A1 | 6/2015 | Carver et al. |
| 2016/0192962 A1 | 7/2016 | Simpson et al. |
| 2016/0199092 A1 | 7/2016 | Patel et al. |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-225349 A | 9/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-78150 A | 4/2009 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO 01/76680 A1 | 10/2001 |
| WO | WO 2006/133030 A2 | 12/2006 |
| WO | WO 2008/029506 A | 3/2008 |
| WO | WO 2008/042987 A2 | 4/2008 |
| WO | WO 2008/065600 A2 | 6/2008 |
| WO | WO 2008/086613 A1 | 7/2008 |
| WO | WO 2008/087613 A2 | 7/2008 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2010/039464 A1 | 4/2010 |
| WO | WO2010/056771 A1 | 5/2010 |
| WO | WO 2012/061935 A1 | 5/2012 |

OTHER PUBLICATIONS

Simpson et al.; U.S. Appl. No. 14/424,277 entitled "Balloon atherectomy catheters with imaging," filed Feb. 26, 2015.
Newhauser et al.; U.S. Appl. No. 14/433,786 entitled "Occusion-crossing devices," filed Apr. 6, 2015.
Patel et al.; U.S. Appl. No. 15/162,330 entitled "Atherectomy catheters with longitudinally displaceable drive shafts," filed May 23, 2016.
Spencer et al.; U.S. Appl. No. 15/162,353 entitled "Occlusion-crossing devices, atherectomy devices, and imaging," filed May 23, 2016.
Tachibana et al.; U.S. Appl. No. 15/162,391 entitled "Atherectomy catheter drive assemblies," filed May 23, 2016.
Gupta et al.; U.S. Appl. No. 14/776,749 entitled "Tissue collection device for catheter," filed Sep. 15, 2015.
Smith et al.; U.S. Appl. No. 14/776,750 entitled "Chronic total occlusion crossing devices with imaging," filed Sep. 15, 2015.
Smith et al.; U.S. Appl. No. 14/776,748 entitled "Optical pressure sensor assembly," filed Sep. 15, 2015.
Simpson et al.; U.S. Appl. No. 14/899,877 entitled "Occusion sheath for imaging catheter," filed Dec. 18, 2015.
Simpson et al.; U.S. Appl. No. 14/899,893 entitled "Identification of elastic lamina to guide interventional therapy," filed Dec. 18, 2015.
Aziz et al.; Chronic total occlusions—a stiff challenge requiring a major breakthrough: is there light at the end of the tunnel?; Heart; vol. 91; suppl. III; pp. 42-48; Jun. 2005.
Emkey et al.; Analysis and evaluation of graded-index fiber-lenses; Journal of Lightwave Technology; vol. LT-5; No. 9; pp. 1156-1164; Sep. 1987.
Gonzalo et al.; Optical coherence tomography patterns of stent restenosis; Am. Heart J.; 158(2); pp. 284-293; Aug. 2009.
Linares et al.; Arbitrary single-mode coupling by tapered and nontapered grin fiber lenses; Applied Optics; vol. 29; No. 28; pp. 4003-4007; Oct. 1, 1990.

(56) References Cited

OTHER PUBLICATIONS

Sharma et al.; Optical coherence tomography based on an all-fiber autocorrelator using probe-end reflection as reference; CWJ13; San Francisco, California; CLEO May 16, 2004; 4 pages.

Suparno et al.; Light scattering with single-mode fiber collimators; Applied Optics; vol. 33; No. 30; pp. 7200-7205; Oct. 20, 1994.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Gupta et al.; U.S. Appl. No. 14/401,175 entitled "Atherectomy catheters with imaging," filed Nov. 14, 2014.

Tachibana et al.; U.S. Appl. No. 14/400,151 entitled "Atherectomy catheter drive assemblies," filed Nov. 10, 2014.

| Low Ref Power | Ref Power | Sample Power | Shot Noise | Thermal Noise | Excess Noise | Total Noise | SNR | SNR (dB) | SNL-SNR | (dB) | SNR Degradation |
|---|---|---|---|---|---|---|---|---|---|---|---|
| -7.60 | 2.51E-08 | 2.5E-09 | 1.61E-22 | 3.31E-22 | 1.01E-23 | 5.02E-22 | 2.50E+05 | 5.40E+01 | 7.80E+05 | 5.89E+01 | 4.94E+00 |
| -7.40 | 3.98E-08 | 2.5E-09 | 2.55E-22 | 3.31E-22 | 2.54E-23 | 6.12E-22 | 3.25E+05 | 5.51E+01 | 7.80E+05 | 5.89E+01 | 3.80E+00 |
| -7.20 | 6.31E-08 | 2.5E-09 | 4.04E-22 | 3.31E-22 | 6.38E-23 | 7.99E-22 | 3.95E+05 | 5.60E+01 | 7.80E+05 | 5.89E+01 | 2.96E+00 |
| -7.00 | 1.00E-07 | 2.5E-09 | 6.41E-22 | 3.31E-22 | 1.60E-22 | 1.13E-21 | 4.42E+06 | 5.64E+01 | 7.80E+05 | 5.89E+01 | 2.47E+00 |
| -6.80 | 1.58E-07 | 2.5E-09 | 1.02E-21 | 3.31E-22 | 4.03E-22 | 1.75E-21 | 4.53E+05 | 5.66E+01 | 7.80E+05 | 5.89E+01 | 2.36E+00 |
| -6.60 | 2.51E-07 | 2.5E-09 | 1.61E-21 | 3.31E-22 | 1.01E-21 | 2.95E-21 | 4.25E+05 | 5.63E+01 | 7.80E+05 | 5.89E+01 | 2.63E+00 |
| -6.40 | 3.98E-07 | 2.5E-09 | 2.55E-21 | 3.31E-22 | 2.54E-21 | 5.42E-21 | 3.67E+05 | 5.56E+01 | 7.80E+05 | 5.89E+01 | 3.27E+00 |
| -6.20 | 6.31E-07 | 2.5E-09 | 4.04E-21 | 3.31E-22 | 6.38E-21 | 1.08E-20 | 2.93E+05 | 5.47E+01 | 7.80E+05 | 5.89E+01 | 4.25E+00 |

FIG. 3C

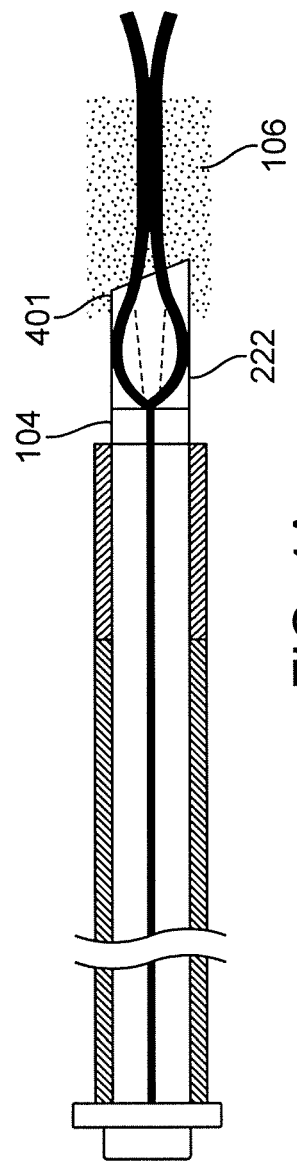

OPTICAL COHERENCE TOMOGRAPHY WITH GRADED INDEX FIBER FOR BIOLOGICAL IMAGING

CROSS REFERENCE TO RELATED APPLICATIONS

This application claims priority to U.S. Application No. 61/646,783, titled "OPTICAL COHERENCE TOMOGRAPHY WITH GRADED INDEX FIBER FOR BIOLOGICAL IMAGING," filed May 14, 2012, which is incorporated by reference in its entirety.

This application may be related to U.S. application Ser. No. 12/790,703, titled "OPTICAL COHERENCE TOMOGRAPHY FOR BIOLOGICAL IMAGING," filed May 28, 2010, which is incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are imaging devices and systems for use in biological probes. In particular, described herein are catheter-based imaging systems using Optical Coherence Tomography (OCT).

BACKGROUND

In intravascular surgery, as well as other medical applications, there is frequently a need to extend very thin (few millimeter diameter), long (30-150+ cm), and sterile catheters into thin-walled (e.g., 1-1.5 millimeter wall thickness) biological lumens, including blood vessels such as arteries and veins.

A number of vascular diseases, such as coronary artery disease and peripheral vascular disease, are caused by the build-up of atherosclerotic deposits (plaque) in the arteries, which limit blood flow to the tissues that are supplied by that particular artery. Disorders caused by occluded body vessels, including coronary artery disease (CAD) and peripheral artery disease (PAD) may be debilitating and life-threatening. Chronic Total Occlusion (CTO) can result in limb gangrene, requiring amputation, and may lead to other complications and eventually death. Increasingly, treatment of such blockages may include interventional procedures in which a guidewire is inserted through a catheter into the diseased artery and threaded to the blocked region. There the blockage may be either expanded into a more open position, for example, by pressure from an inflated catheter balloon (e.g., balloon angioplasty), and/or the blocked region may be held open by a stent. Treatment of such blockages can also include using a catheter to surgically remove the plaque from the inside of the artery (e.g., an atherectomy).

There is medical interest in equipping catheters with sensors that can help direct the catheter for atherectomy, occlusion-crossing, and/or other surgical procedures. For example, it would be useful to have sensors that can give the surgeon immediate visual feedback as to whether a particular tissue is diseased and/or how far away the cutting portion of a catheter is from the boundary of a particular blood vessel layer to minimize the risk of accidental damage.

Conventional radiological imaging methods and ultrasound imaging systems have been attempted for such surgical procedures. However, neither ultrasound nor radiological imaging methods have enough resolution to help guide the operation of the catheter through small dimensions. Moreover, standard radiological techniques cannot easily discriminate between healthy tissue and diseased tissue unless the tissue has become heavily calcified. Further, the components of an ultrasound system are generally too large to implement on a small scale, such as with a system configured to be used within blood vessels.

Optical Coherence Tomography (OCT) has been proposed as one technique that may be particularly helpful for imaging regions of tissue, including within a body lumen such as a blood vessel. At a basic level, OCT relies on the fact that light traveling from a source and scattering from more distant objects takes longer to travel back than light scattering from nearby objects. Due to the wave nature of light, very small timing differences caused by light signals traveling different distances on the micron scale can cause constructive or destructive interference with reference light signals. OCT systems measure the resulting interference to obtain an image of the target. A typical OCT system requires one or more interferometers to distinguish the signal from the applied light. In addition, most known OCT systems, when applied to catheters, include a fiber that is rotated (often at high rates) within the catheter in order to scan the lumen and a second, large reference arm.

Referring to FIG. 1, a typical OCT device includes a target arm and a reference arm to generate a reference signal. In order to provide the interference reference signal, the OCT device will split an illuminating light signal from the source in two equal or unequal parts, send part of the illuminating light to the target of interest through one target optical "target arm" and send the other part of the illuminating light down a separate reference arm. Light from the separate reference arm reflects off of a mirror, and then returns and interferes with the scattered light that is returning from the target optical arm after bouncing off of the target. In a traditional OCT device, the reference arm length is engineered to be exactly the same length as the target arm so that the interference effect is maximized. The resulting interference between the two beams creates interference that can be measured to extract depth information related to the target. Using this depth information, an image of the object can be generated. Referring still to FIG. 1, a typical OCT device can further include a focusing lens in the target arm, such as a graded index (GRIN) lens, configured to focus the light coming out of the optical fiber into the tissue.

These traditional OCT systems, however, are large and cumbersome due to the required reference arm and are therefore generally ineffective for use in a medical catheter, particularly for use with a low cost and disposable catheter. Using a common path OCT system, i.e., a system without a separate reference arm, is one way to eliminate the cost and size of such an imaging catheter. There are several challenges, however, associated with developing a catheter having common path OCT. For example, a common path OCT system requires that the reference reflection be formed within the same optical conduit as the target reflection. This reference reflection must be finely tuned to avoid noise in the system, requiring that the path from the light source to the reflection interface be free of unnecessary components, such as focusing elements, that could interfere with the reference reflection. Further, the common path system must have components that are small enough to fit inside of a single small catheter, making it difficult to include additional components. Finally, for common path OCT, it is desirable to have the reference reflection as close to the tissue as possible to maintain the imaging range within the coherence length of the source and avoid data processing burden, as data processed for the distance between the reference and the start of the imaging is not useful. Accordingly, a common path OCT system that solves some of these problems is desired.

SUMMARY OF THE DISCLOSURE

In general, in one embodiment, a system for optical coherence tomography includes a source of optical radiation, an optical fiber, and a graded index fiber attached to a distal end of the optical fiber. The optical fiber and the graded index fiber are together configured to provide a common path for optical radiation reflected from a reference interface at a distal end of the graded index fiber and from a target. The system further includes receiving electronics configured to receive the optical radiation reflected from the reference interface and the target and a processor to generate an image of the target based upon the optical radiation received by the receiving electronics.

This and other embodiments can include one or more of the following features. A secondary reflection of optical radiation from an interface between the optical fiber and the graded index fiber can be less than −60 dB. The reference interface can provide a reference reflection of between −28 and −42 dB. The system can further include an interface medium at the reference interface that can be in optical contact with the graded index fiber. A refractive index of the graded index fiber and a refractive index of the reference medium can be mismatched such that the receiving electronics operate in a total noise range that can be within 5 dB of the shot noise limit. The reference interface can be angled with respect to a longitudinal axis of the graded index fiber such the receiving electronics can operate in a total noise range that is within 5 dB of the shot noise limit. A surface of the interface medium that is closest to the target can be concave. The interface medium can be an adhesive. An outer diameter of the graded index fiber and a protective coating around the graded index fiber can be less than 0.01 inches.

In general, in one embodiment, a system for optical coherence tomography includes a source of optical radiation, an optical fiber, and a graded index fiber attached to a distal end of the optical fiber. The optical fiber and the graded index fiber are together configured to provide a common path for optical radiation reflected from a reference interface at a distal end of the graded index fiber and from a target. The system further includes receiving electronics configured to receive the optical radiation reflected from the reference interface and the target and a processor to generate an image of the target based upon the optical radiation received by the receiving electronics. A secondary reflection of optical radiation from an interface between the optical fiber and the graded index fiber is less than −60 dB.

This and other embodiments can include one or more of the following features. The reference interface can provide a reference reflection of between −28 and −42 dB. The system can further include an interface medium at the reference interface that can be in optical contact with the graded index fiber. A refractive index of the graded index fiber and a refractive index of the reference medium can be mismatched such that the receiving electronics operate in a total noise range that can be within 5 dB of the shot noise limit. The reference interface can be angled with respect to a longitudinal axis of the graded index fiber such the receiving electronics can operate in a total noise range that is within 5 dB of the shot noise limit. A surface of the interface medium that is closest to the target can be concave. The interface medium can be an adhesive. An outer diameter of the graded index fiber and a protective coating around the graded index fiber can be less than 0.01 inches.

In general, in one embodiment, a catheter for use with optical coherence tomography includes an elongate catheter body. The catheter includes an optical fiber in the elongate catheter body and a graded index fiber attached to a distal end of the optical fiber. The optical fiber and the graded index fiber are together configured to provide a common path for optical radiation reflected from a reference interface at a distal end of the graded index fiber and a target. A secondary reflection of optical radiation from an interface between the optical fiber and the graded index fiber can be less than −60 dB.

This and other embodiments can include one or more of the following features. The reference interface can provide a reference reflection of between −28 and −42 dB. A distance from an outer edge of the elongate catheter body and a focal point of the GRIN lens can be less than 1 mm. A distance from an outer edge of the elongate catheter body and a focal point of the GRIN lens can be less than 0.8 mm. The catheter can have a diameter of approximately 2 mm. The focal point can be configured to be in the target. The elongate catheter body can be an atherectomy catheter. The elongate catheter body can be an occlusion crossing catheter having a rotatable tip and a guidewire lumen therein.

In general, in one embodiment, a method of imaging a target includes inserting a catheter into a lumen of the target; transmitting optical radiation from a source through an optical fiber and a graded index fiber within the catheter; transmitting the optical radiation from the graded index fiber through an interface medium; transmitting the optical radiation reflected from the target and reflected from a reference interface along a common path in the graded index fiber and the optical fiber to a detector; and generating an imaging of the target based upon the reflected optical radiation.

This and other embodiments can include one or more of the following features. A distance from an edge of the catheter and a focal point of the graded index fiber can be less than 0.8 mm. The focal point can be in the target.

In general, in one embodiment, a method of making a graded index fiber for use with a common path optical coherence tomography system includes selecting a required distal angle of the graded index fiber such that a reference interface at the distal end of the graded index fiber will produce a reference reflection of between −28 and −42 dB; and polishing or cleaving the distal end of the graded index fiber to the selected angle within a tolerance of less than 0.2°.

This and other embodiments can include one or more of the following features. The method can further include splicing a graded index fiber to a distal end of a single mode optical fiber. The method can further include placing the distal end of the graded index fiber in optical contact with an interface medium to form the reference interface. The method can further include making an external surface of the interface medium concave.

BRIEF DESCRIPTION OF THE DRAWINGS

FIG. 3C shows a chart including data drawn from the graphs in FIGS. 3A and 3B.

FIG. 4A shows an exemplary optical fiber having a GRIN fiber cleaved/polished at an angle and the tip inserted into a medium of known refractive index.

DETAILED DESCRIPTION

The Optical Coherence Tomography (OCT) catheters and systems described herein are configured to provide image guided intra-vascular procedures that may be particularly useful for the diagnosis and/or treatment of arterial disease. The systems may include a catheter, an umbilical connection, and a console. The system uses OCT to form an image of the intravascular environment close to the catheter cutter. During intraluminal procedures, such as atherectomy, problems can arise as a result of failure to properly identify target tissue. By using a catheter having a common path optical fiber for OCT, proper identification of target tissue can be improved.

In general, the catheters described herein include a common-path system with a graded index (GRIN) fiber attached to the distal tip of a single mode optical fiber in the catheter so as to act as a lens for focusing light. The distal portion of the GRIN fiber is modified to provide a reference reflection between −28 dB and −45 dB, such as −28 dB and −42 dB, −32 dB and −45 dB, or −32 and −42 dB. In some embodiments, a secondary reflection of optical radiation from an interface between the optical fiber and the graded index fiber is configured to be less than −60 dB. An outer diameter of the graded index fiber and a protecting coating around the graded index fiber can be less than 0.01 inches. This common path OCT system with GRIN fiber advantageously achieves focusing of the light beam while still achieving the desired stable reference reflection and maintaining a small profile of the catheter.

Figure 1:
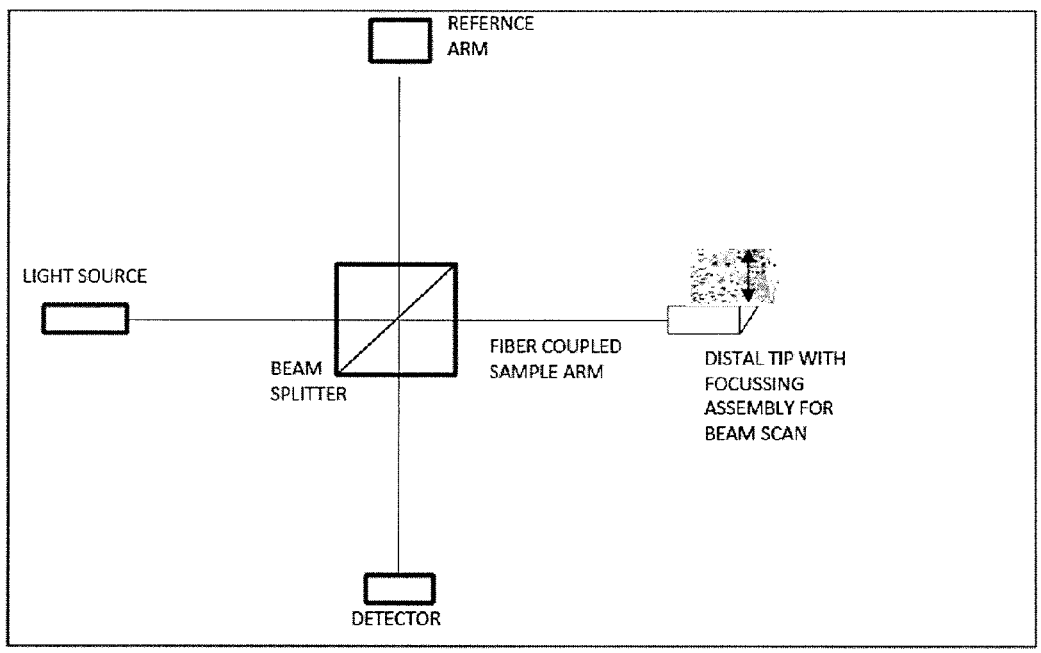
FIG. 1 shows an example of a prior art OCT system.
Figure 2A:
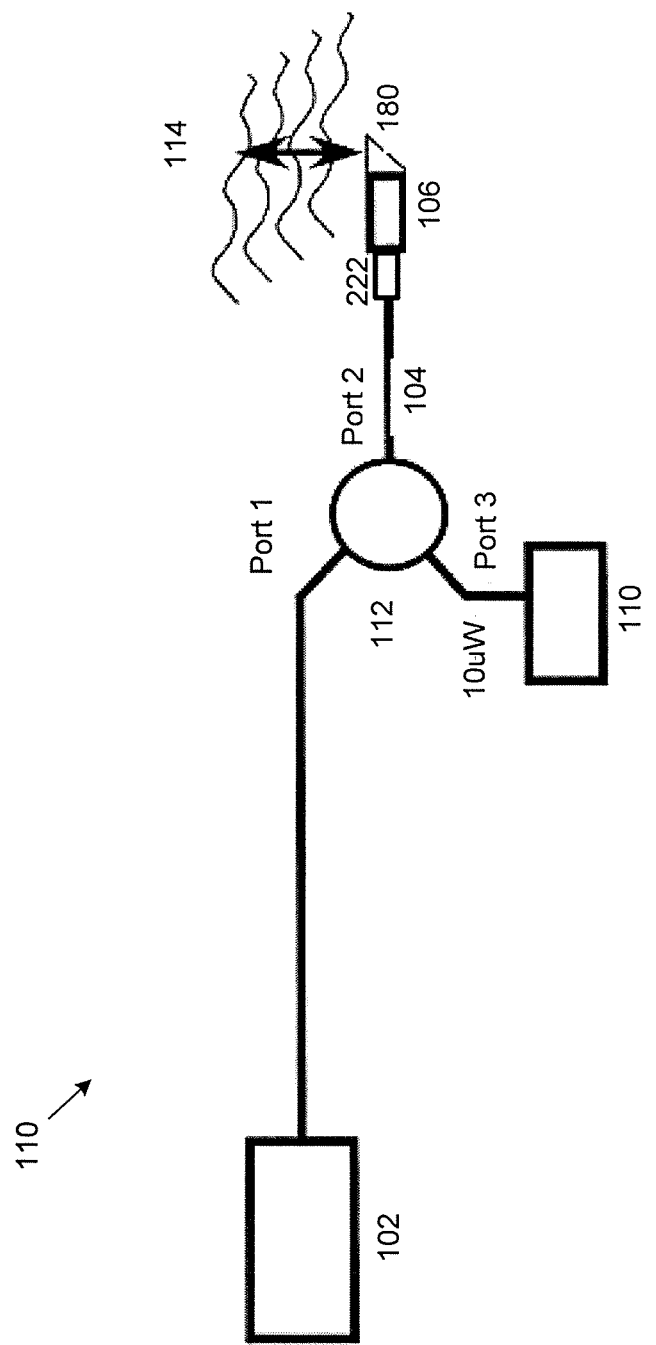
FIG. 2A shows an exemplary OCT system as described herein.

Referring to FIG. 2A, a common-path OCT system 100 includes a laser source 102, such as a swept frequency light source. An optical fiber 104, such as a single mode optical fiber, transfers radiation from the laser source 102 towards the target 114. A graded index fiber ("GRIN fiber") 222 is attached to the distal end of the optical fiber 104. Further, the GRIN fiber 222 is in optical contact with an interface medium 106, such as an adhesive, epoxy, or cement. The light exiting the GRIN fiber 222 is thus in optical contact with the interface medium 106 such that the light exiting the GRIN fiber 222 and entering the interface medium 106 sees only a single interface. In some embodiments, the GRIN fiber 222 is embedded in the interface medium 106.

In the common-path OCT system 100, the index of refraction of the interface medium 106 is different than the index of refraction of the distal edge of the GRIN fiber 222. Because the indices of refraction of the interface medium 106 and the distal edge of the GRIN fiber 222 are different, a Fresnel reference reflection can be created, which can be used to generate the resulting OCT image. That is, part of the light from the light source will exit the GRIN fiber 222 to travel to the target 114 while part of the light will be reflected back from the distal end of the GRIN fiber 222 to form the reference reflection for the OCT system. Some of the light beam that exits the GRIN fiber 222 will encounter the target 114 and be reflected or scattered by the target 114, and some of this scattered light will, in turn, reenter the distal end of the GRIN fiber 222 and interfere with the reference reflection. The interference signal then travels back through the fiber 104. A Faraday isolation device 112, such as a Faraday Effect optical circulator, can be used to separate the paths of the outgoing light source signal (i.e., the light being sent to the target from the light source) and the interference signals returning from the distal end of the fiber. The separated interference signal can travel back to a detector 110 located at the proximal end of the optical fiber 104. The interference signal detected by the detector 110 can then be used create an image of the target, as described below.

Because the reflected or scattered target light in the OCT system 100 travels a longer distance than the Fresnel reflected reference light, the reflected or scattered target light can be displaced by frequency, phase and or time with respect to the reference beam. For example, if swept-source radiation is used, then the light from the target will be displaced in frequency. The difference in displacement in phase, time or frequency between the reflected or scattered target light and the reference light can be used to derive the path length difference between the end of the optical fiber tip and the light reflecting or light scattering region of the target. In the case of swept source OCT, the displacement is encoded as a beat frequency heterodyned on the carrier reference beam. Embodiments such as the system described with respect to FIG. 2A, where the light paths in the reference and signal arms are common, are called common path interferometers. Using common path interferometry helps provide a low cost disposable catheter, as it eliminate the separate reference arm without adding significant size or system requirements to the catheter itself.

Figure 2B:
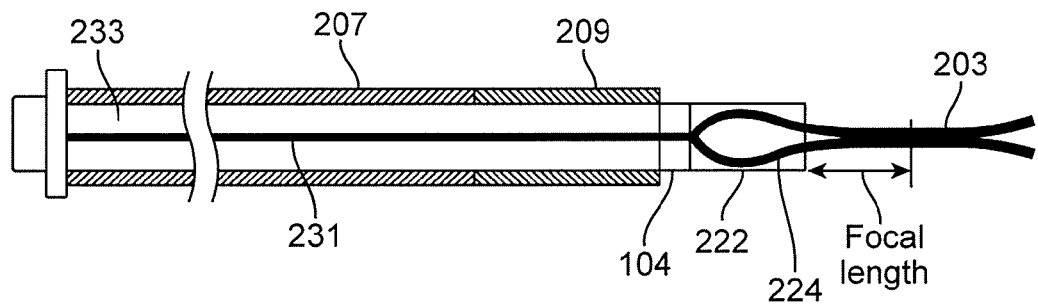
FIG. 2B shows the travel of light through and out of a GRIN fiber.

Referring to FIG. 2B, the GRIN fiber 222 can be spliced, such as fusion spliced, onto the distal end of the optical fiber 104. As shown in FIG. 2B, the core 224 of the GRIN fiber 222 is much larger than the core 231 of the optical fiber 104 in order to allow the light to be expanded and contracted properly within the core of the GRIN fiber 222. For example, the diameter of the core 224 of the GRIN fiber 222 can be greater than 40 µm, such as greater than 50 µm, such as greater than 60 µm, such as 40-110 µm, e.g., approximately 100 µm, while the diameter of the core 231 of the optical fiber 104 can be less than 20 µm, such as less than 10 µm, such as 8-10 µm, e.g., approximately 9 µm. The GRIN fiber 222 can be spliced in such a manner so as to minimize any return loss caused by the transition from the optical fiber 104 to the GRIN fiber 222, i.e., to prevent a ghost image from forming due to a secondary reflection caused at the interface between the optical fiber 104 and the GRIN fiber 222. For example, the optical fiber 104 and the GRIN fiber 222 can be spliced together at an angle. In one embodiment, the secondary reflection cause at the interface between the optical fiber 104 and the GRIN fiber 222 is less than or equal to −60 DB.

The GRIN fiber 222, in contrast to standard lenses and even traditional GRIN lenses, can be specifically constructed such that the GRIN fiber 222 (including the core and any cladding, such as a cladding of less than 15 µm, e.g., approximately 12.5 µm) is approximately the same outer diameter as the optical fiber 104 (including the core 231 and cladding 233), thereby helping to maintain a low profile for the common path OCT system. For example, in one embodiment, the combined outer diameter of the optical fiber 104 and the GRIN fiber with a protective coating (as described further below) are both less than 0.01 inches, such as less than 0.08 inches, such as approximately 0.0065 inches with a protecting coating thickness of greater than or equal to 0.007 mm, such as 0.015 mm, 0.02 mm, or 0.022 mm. Advantageously, the GRIN fiber 222, in contrast to a larger focusing lens, can advantageously be substituted in place of a distal portion of an optical fiber in a catheter without having to make significant changes to the catheter design due to the relatively small diameter of the fiber.

Figure 2C:
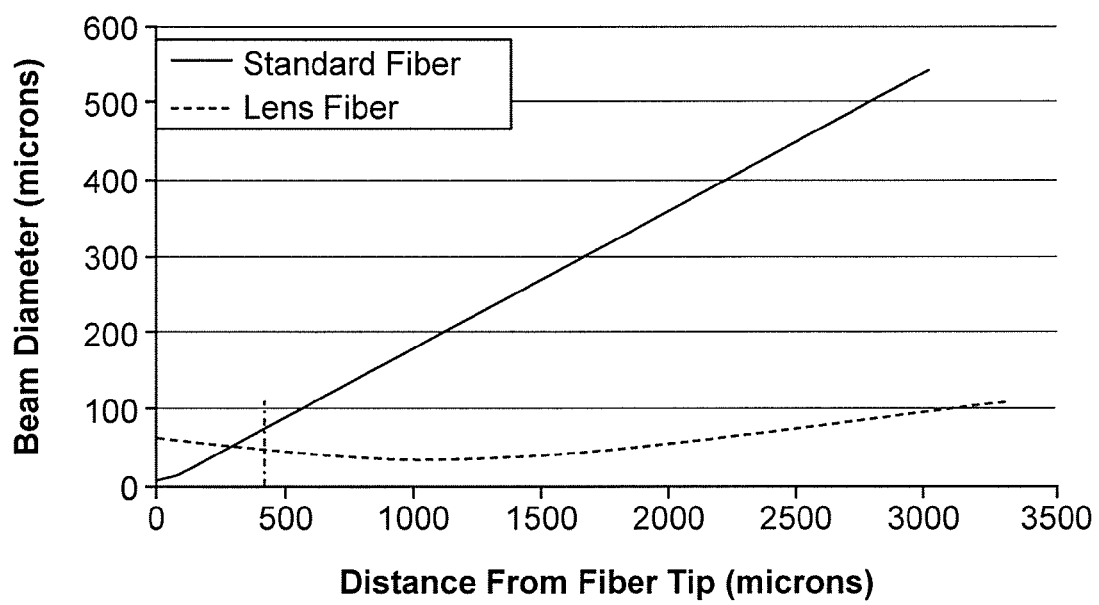
FIG. 2C shows an exemplary graph of the diameter of a light beam as it exits a standard optical fiber vs. exiting a GRIN fiber.
Figure 2D:
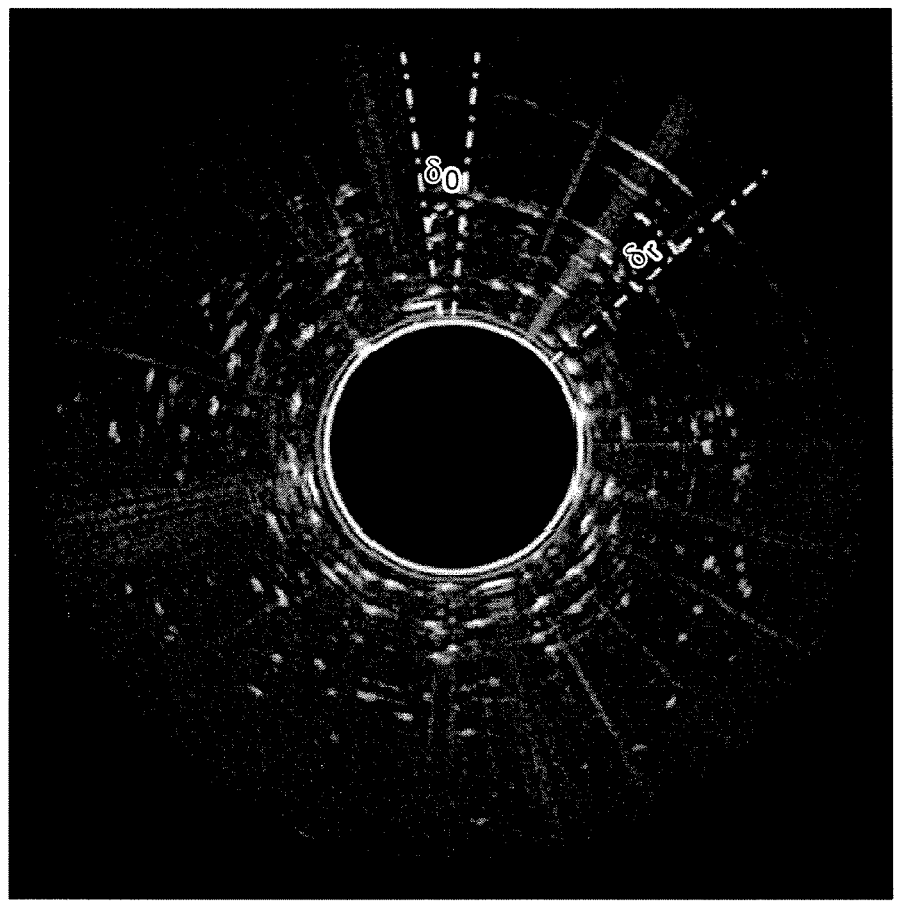
FIG. 2D shows the resolution of an OCT image.

Referring to FIGS. 2B and 2C, the GRIN fiber 222 can advantageously help focus light coming out of the optical fiber 104. That is, as shown in FIG. 2C, light coming out of a standard optical fiber will spread out, thereby lowering the resolution of the resulting OCT image. In contrast, the light coming out of a GRIN fiber will stay at a much smaller diameter throughout the imaging depth of the target and thus increase the resolution of the resulting OCT image. That is, the azimuthal resolution ($\delta_\theta$) will be increased by using a GRIN fiber, which can help maintain the dynamic range with the depth. The azimuthal resolution is defined as minimal feature size which can be accurately represented by the imaging system, as shown in FIG. 2D. The azimuthal resolution is primarily dependent on the beam diameter of the investigating beam. The resolution is at least two times the diameter of the spot size. In one embodiment, the beam diameter of the GRIN fiber at focus (which can be less than 1 mm from the catheter tip, as described further below) is 35±5 microns in contrast to a standard single-mode optical fiber where the light expands outward without focusing (as shown in FIG. 2C). As a result, the minimal resolvable feature size can be reduced to less than 100 microns, such as approximately 70 microns.

Referring back to FIG. 2B, the GRIN fiber 222 can be cleaved at the distal end such that the length of the GRIN fiber 222 allows the light 203 coming out of the GRIN fiber 222 to focus at the required distance or focal length within the area being imaged. For example, the light can focus between 0.5 mm and 1.5 mm, such as approximately 1.1 mm away from the distal tip of GRIN lens. The beam diameter at the focus can be somewhere between 10 and 60 microns, such as between 20 and 40 microns. As described below, the GRIN fiber 222 can be placed within a catheter such that the focal point of the fiber 222 is directly within the target being imaged.

In some embodiments, as shown in FIG. 2B, a coating 207, such as a polyimide coating, covers the optical fiber 104 to strengthen the fiber, such as to withstand the tortuosity within the catheter, and/or protect the fiber 104 from environmental factors such as water vapor. During splicing of the optical fiber 104 and the GRIN fiber 222, part of the coating 207 near the distal end, such as approximately 5 mm from the distal end, of the optical fiber 104 can be removed in order to allow for proper splicing, e.g., to allow the splicing equipment proper access to the fiber 104 and/or to prevent the coating 207 from melting over the distal end of the fiber 104 during splicing. In order to strengthen and protect the optical fiber 104 after splicing, the fiber 104 can be recoated with a recoat layer 209, which can be, for example, polyimide.

Referring back to FIG. 2A, the laser source 102 can operate at a wavelength within the biological window where both hemoglobin and water do not strongly absorb the light, i.e. between 800 nm and 1.4 µm. For example, the laser source 102 can operate at a center wavelength of between about 1300 nm and 1400 nm, such as about 1310 nm to 1340 nm. The optical fiber 104 can be a single mode optical fiber for the ranges of wavelengths provided by the laser source 102. Further, the gradient index profile of the GRIN fiber can be chosen such that the desired spot size is achieved at the desired focal distance. Furthermore, the distal end of the GRIN fiber 222 and the interface medium 106 can have specifically-chosen indexes of reflection such that a known magnitude of reference reflection is created. For example, the indexes of reflection can be chosen such that noise in the OCT system is minimized.

Noise in OCT systems comes from at least three sources: shot noise, thermal or Johnson noise, and residual intensity noise (RIN noise). There may additionally be noise from the analog-to-digital conversion process. RIN noise comes from noise intrinsic to the light source, tends to dominate at high reference powers, and can be limited by limiting the maximum laser light intensity, working with an alternative low RIN light source (non-laser), or by using balanced detection. Thermal (Johnson) noise tends to dominate at low reference power levels, and can be avoided by working at reference power levels yielding a DC photodiode current above that of the thermal noise floor.

Shot noise dominates in between RIN noise and thermal (Johnson) noise. Shot noise is caused by statistical fluctuations in the number of photons or electrons that carry a particular signal. For a well designed system, shot noise is the limiting factor in dynamic range. The indexes of refraction of the GRIN fiber 222 and the interface medium 106 can thus be chosen such that the OCT system 100 operates close to the shot noise limit.

Figure 3A:
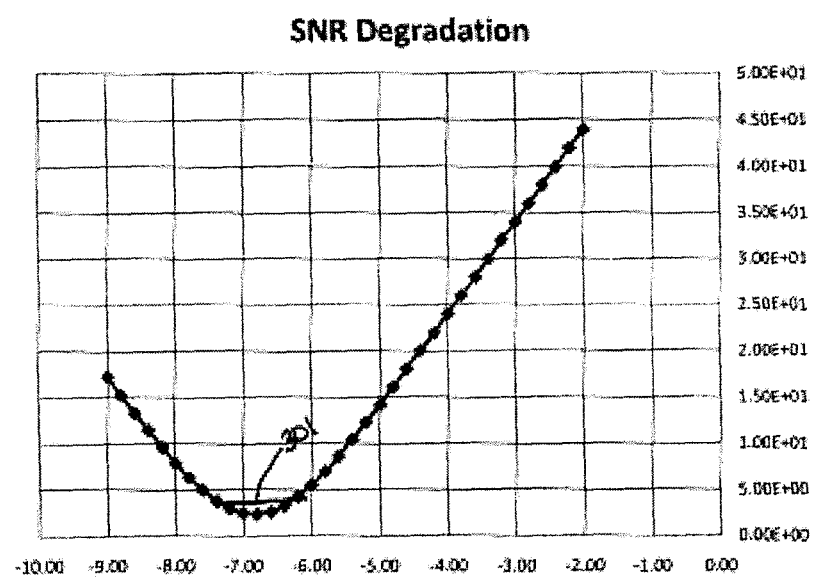
FIG. 3A shows an exemplary graph of noise in an OCT detector vs. power.
Figure 3B:
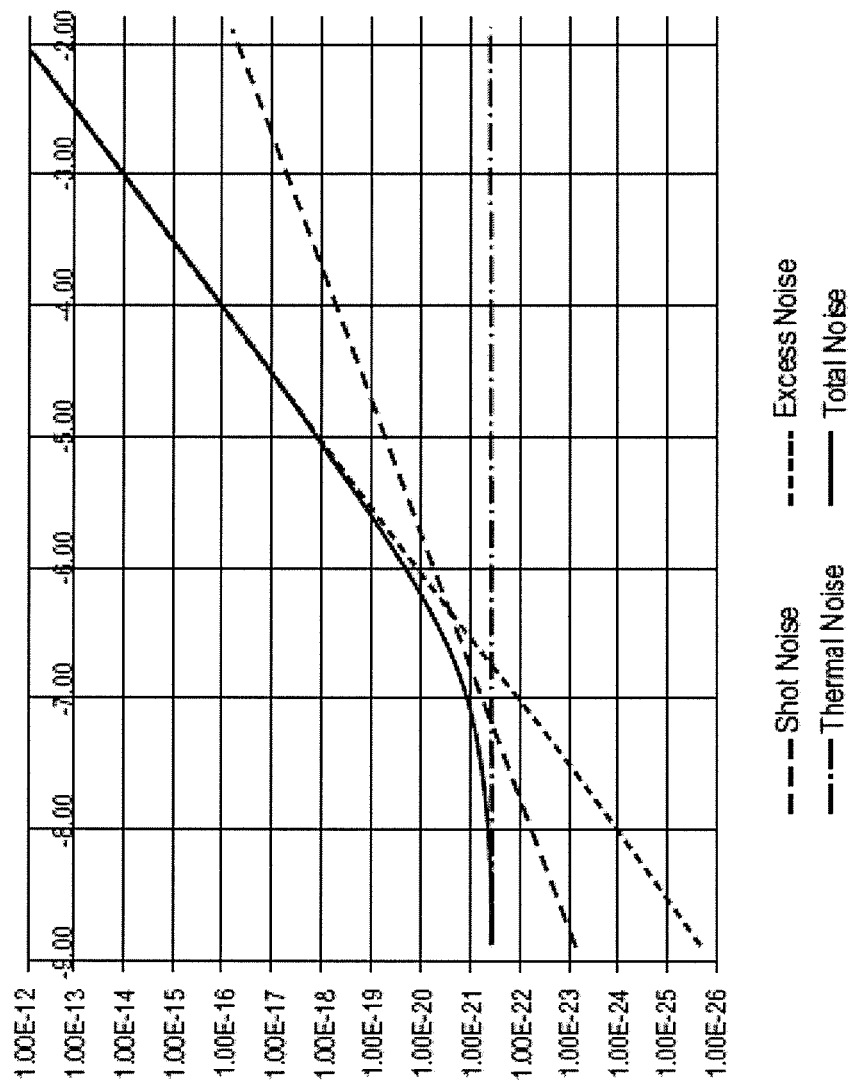
FIG. 3B shows an exemplary graph of a breakdown of the types of noise contributing to the total noise in the graph of FIG. 3A.

The shot noise limit of a particular receiver is set by the responsivity of the photodetector, the detection bandwidth desired, and the reference DC power impinging on the detector element. An exemplary graph of a noise v. power is shown in FIG. 3A with a break-down by the type of noise shown in FIG. 3B. The graphs in FIGS. 3A and 3B assume a system having 10 mW of forward power, 1550 nm center wavelength, 20 nm bandwidth, 1 MHz detection bandwidth, and a 1 A/W responsivity.

The shot noise limit is the area 301 at the bottom of the curve in FIG. 3A, at which the noise is the lowest or where the degradation from the shot noise limit is the least. Using the graph for a particular receiver, such as the graphs shown in FIG. 3A and FIG. 3B, the desired power at the detector, $P_{det}$, can be determined that would place the noise within a desired range of the shot noise limit. For example, FIG. 3C shows a table of values drawn from FIG. 3B. Referring to FIG. 3C, a power of 0.158 µW would place the receiver at the minimum degradation point, 2.36 dB above the shot noise limit. Moreover, reference powers of between 63.1 nW and 251 nW would place the noise within 3 dB of the shot noise limit. Reference powers of between about 25 nW to 0.631 µW would place the noise within 5 dB of the shot noise limit.

To determine the total power, $P_{out}$, that must be reflected from the interface 106 to obtain the desired $P_{det}$, the losses of the detector 110 must be taken into account according to Equation 1:

$$P_{det} = P_{out}(1-L) \quad \text{(equation 1)}$$

where $P_{out}$ is the power reflected from the reference interface and L is the sum of the optical losses from the distal end of the probe to the detector 110. Therefore, assuming that $P_{det}$ is equal to 0.2 µW (rounding from the 0.158 µW determined to place the noise as low to the shot noise limit as possible) and that the intermediate optical system operates at 90% efficiency such that L is 10%, then $P_{out}$ is equal to 0.2 µW/(0.9)=0.222 µW.

The forward power at the distal end of the GRIN fiber prior to entering the interface medium is given by $P_{in}$. In one exemplary embodiment, $P_{in}$ can be equal to 10 mW.

Moreover, $P_{out}$ and $P_{in}$ can be used to determine the reflectivity of the reference interface 180, according to equation 2:

$$P_{out} = P_{in} R^2 \quad \text{(equation 2)}$$

where R is the Fresnel coefficient of reflectivity. Therefore, assuming that $P_{out}$ is 0.2222 µW and $P_{in}$ is 10 mW (as described above), then R is equivalent to 0.004714.

Moreover, the Fresnel equation (shown by equation 3) governs the intensity of reflection from a normal or near normal interface:

$$R = \left(\frac{n_1 - n_2}{n_1 + n_2}\right) \quad \text{(equation 3)}$$

where the index of refraction of the transparent medium is given by $n_2$ and that of the core is $n_1$.

If the distal end of the GRIN fiber 222 is kept polished such that it has a normal interface with the interface medium, then the refractive index of the GRIN lens, $n_1$, will be fixed and can be assumed to be substantially equal to the refractive index at the center of the GRIN lens. For example, if the refractive index at the center of the GRIN lens is 1.4677, then the refractive index of the interface medium $n_2$ would have to be 1.4816 or 1.4539, according to equation 3 above. Thus, an interface medium of either index will produce the desired reference reflection. In some embodiments, the medium with the higher index of refraction may be preferable as it may be more readily available and/or have better mechanical properties, such as tensile strength.

The interface medium used with system 100 can be, for example, an adhesive. Depending upon the required index of refraction, the interface medium can be, for example, M21-CL which is a thermal curing adhesive. Another exemplary interface medium is the Light Weld® UV curable photonics adhesive OP-4-20658, produced by Dymax corporation, Torrington Conn. This adhesive, which has a refractive index of 1.585 in the cured state, is a rigid clear UV-curable adhesive that can be applied in a liquid form, and which then cures to a rigid form within seconds of exposure to UV light. Another exemplary transparent medium is EpoTek OG127-4 or OG116, produced by Epoxy Technology, Billerica Mass. This has a refractive index of 1.602 in the cured state. Another exemplary transparent medium is Masterbond EP42HT-2, which has a cured refractive index of 1.61. Another exemplary transparent medium is Norland Optical Adhesive NOA-61, which has a refractive index of 1.56 upon curing.

If an interface medium having the exact refractive index desired cannot be found (for example because it does not have the proper tensile strength or is not biocompatible), an interface medium having a refractive index that is close can be selected and the power in, $P_{in}$, can be adjusted accordingly. Using the known r and the desired power at the detector, $P_{det}$, the required power in $P_{in}$ can then be determined according to equation 4:

$$P_{det} = P_{in} R^2 (1-L) \quad \text{(equation 4)}$$

In some implementations, the interface medium can be applied in a semi-liquid state, such as by dispenser, ink jet deposition, spraying, painting, dipping, or other process. The medium may then be cured to a solid form, such as by UV curing, thermal curing, chemical curing, drying, or other process. Other processes, such as vacuum deposition of transparent medium or direct mechanical placement of the transparent medium may also be used.

The interface medium can have a minimum thickness (i.e. depth between the end of the optical fiber and the end of the interface medium) of at least $$\frac{\lambda_{min}}{2\pi},$$

where $\lambda_{min}$ is the wavelength of light in the optical fiber. For a wavelength of over 1250 nm, this will be approximately 200 nm or greater. The interface medium can also have a thickness that is great enough to introduce an offset between the reference reflection and the minimum distance that the target can approach the distal exit face of the GRIN fiber 222.

Figure 3D:
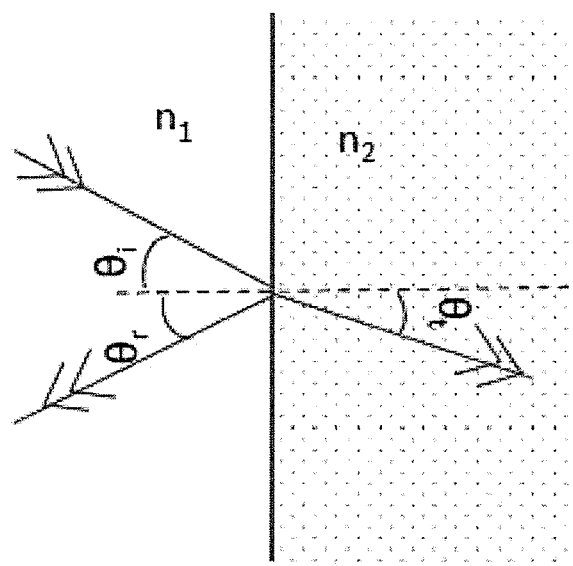
FIG. 3D shows the angles associated with a light beam at an interface of two separate mediums with different refractive indices.

Alternatively, if a particular interface medium is desired due, for example, to the adhesive properties and/or biocompatibility of the interface medium, then the desired reference reflection can be achieved by cleaving or polishing the distal end of the GRIN fiber at a particular angle. In this case, equation 5 governs the reflection from the surface assuming that the incident light is unpolarized and therefore contains an equal mix of s and p polarizations:

$$R = \left|\frac{R_S + R_P}{2}\right| \quad \text{(equation 5)}$$

where Rs is the reflection coefficient caused by the s-polarized light and is determined by equation 6:

$$R_S = \left|\frac{n_1 \cos\theta_i - n_2 \cos\theta_t}{n_1 \cos\theta_i - n_2 \cos\theta_t}\right| \quad \text{(equation 6)}$$

where is $\theta_i$ is the angle of incidence and $\theta_t$ is the angle of transmittance (see FIG. 3D). Further, as shown in FIG. 3D, $\theta_r$ is the angle of reflection. Further, Rp in equation 5 is the reflection coefficient caused by the p-polarized light and is determined by equation 7:

$$R_P = \left|\frac{n_1\cos\theta_t - n_2\cos\theta_i}{n_1\cos\theta_t - n_2\cos\theta_i}\right|$$ (equation 7)

Accordingly, if the refractive index of the medium, $n_2$, is fixed because a particular medium is desired, then the Fresnel reflection can be adjusted by changing the cleave or polishing angle of the distal end of the GRIN fiber. In some embodiments, the cleave or polishing angle can be cleaved or polished to the desired angle within a tight tolerance, such as a tolerance (or variation from the desired angle) within less than 0.5°, less than 0.4°, less than 0.3°, or less than 0.2°, such as less than or equal to 0.15°. In contrast to standard single mode fibers, cleaving or polishing the distal end of the GRIN fiber within such tight tolerances is important to obtain the desired index of reflection because the back-reflection in GRIN fiber is much more sensitive to the cleave angle than the back-reflection in standard single-mode fiber.

Thus, as shown in FIG. 4A, the GRIN fiber 222 can be cleaved or polished at the distal end 401, thereby providing the appropriate Fresnel coefficient of reflectivity. For example, the angle can be less than 4 degrees, less than 2 degrees, or less than 1 degree (plus or minus the tight tolerance as described above). In one embodiment, the combination of the angle between the interface medium 106 and the GRIN fiber 222 and the mismatch between the two refractive indices gives −28 dB and −45 dB, such as −28 dB and −42 dB, −32 dB and −45 dB, or −32 and −42 dB return loss.

Once the approximate angles have been determined using the equations described herein, the polishing can be adjusted slightly to compensate for any loss of light caused by the interface between the GRIN fiber and the optical fiber. That is, the Fresnel equations described herein do not take into account the interface between the GRIN fiber and the optical fiber. If the distal end of the GRIN fiber is polished or cleaved at an angle, then the coupling efficiency of resulting beam of reflected light traveling through the GRIN fiber and into the Single Mode optical fiber may change. Thus, while the distal angle required can be approximately determined by the equations described herein, further adjustment may be required in order to achieve the desired reflection. Further, the tolerance on the set angle for required reference reflection is very high as a the magnitude of change in reference reflection is effected both by Fresnel Reflection and coupling efficiency of the light from GRIN fiber into the Single Mode optical fiber. In some embodiments, additional factors, such as the diameter of the GRIN fiber, can also be adjusted to achieve the desired reflection. The device described herein can thus include a GRIN fiber as a focusing element that generates a stable reference reflection at the distal tip of the GRIN fiber.

Figure 4B:
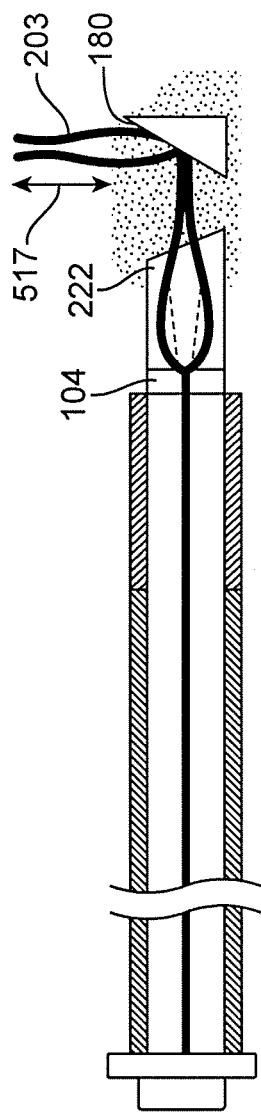
FIG. 4B shows the light path in the system of FIG. 4A as it is reflected from a reflective surface in a catheter.

Referring to FIG. 4B, a reflective surface 180, such as an angled mirror (e.g., angled at 35-55 degrees relative to the axis of the optical fiber, such as 45 degrees), can be used to deflect the 203 beam in the desired orientation (such as into adjacent tissue). As shown in FIG. 4B, the focus of the beam 203 can be within the tissue (after reflecting off of the reflective surface 180).

Figure 5A:
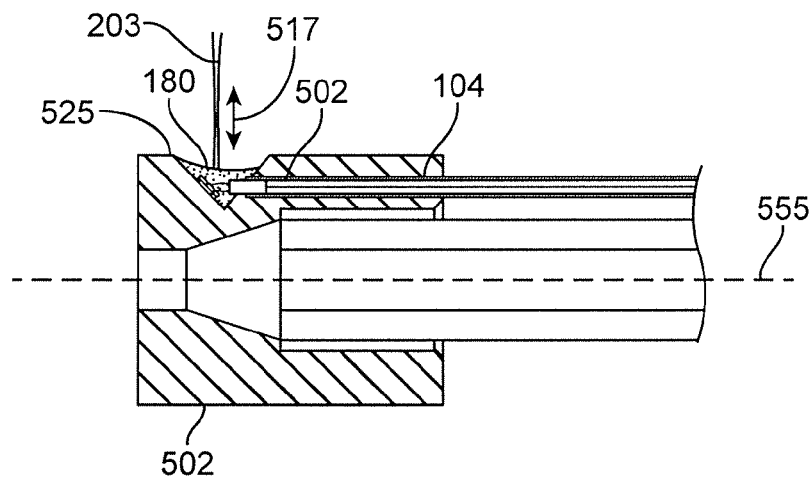
FIG. 5A shows the use of an optical fiber with a GRIN lens in an OCT catheter.
Figure 5B:
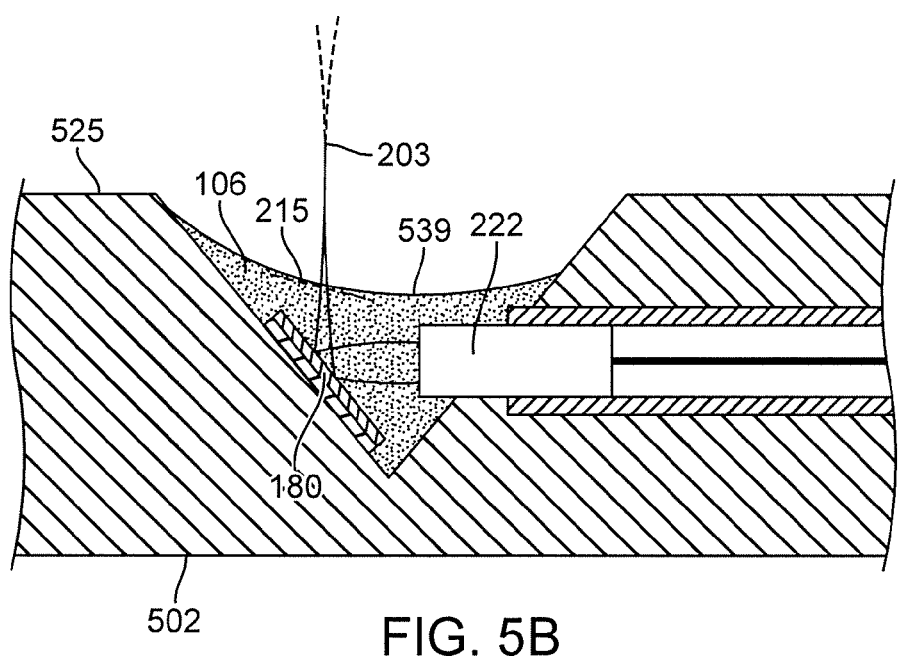
FIG. 5B shows a close-up of the distal end of the GRIN fiber of FIG. 5A.

Referring to FIGS. 5A and 5B, the imaging system described herein can be used with a catheter, such as an atherectomy catheter or an occlusion crossing catheter. The atherectomy catheter can have a cutting tip and a tissue storage chamber. The occlusion crossing device can have a rotatable tip and a guidewire lumen. Exemplary catheters with which the imaging systems described herein can be used are described in copending Patent Applications: U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; U.S. patent application Ser. No. 13/433,049, titled "OCCLUSION-CROSSING DEVICES, IMAGING, AND ATHERECTOMY DEVICES," filed Mar. 28, 2012, Publication No. US-2012-0253186-A1; International Patent Application titled "OCCLUSION-CROSSING DEVICES," filed herewith; International Patent Application titled "CHRONIC TOTAL OCCLUSION CROSSING DEVICES WITH IMAGING," filed herewith; U.S. patent application Ser. No. 12/829,277, titled "ATHERECTOMY CATHETER WITH LATERALLY-DISPLACEABLE TIP," filed Jul. 1, 2010, Publication No. US-2011-0004107-A1; U.S. patent application Ser. No. 13/175,232, titled "ATHERECTOMY CATHETERS WITH LONGITUDINALLY DISPLACEABLE DRIVE SHAFTS," filed Jun. 1, 2011, Publication No. US-2012-0046679-A1; U.S. patent application Ser. No. 13/654,357, titled "ATHERECTOMY CATHETERS AND NON-CONTACT ACTUATION MECHANISM FOR CATHETERS," filed Oct. 17, 2012; U.S. patent application Ser. No. 13/675,867, titled "OCCLUSION-CROSSING DEVICES, ATHERECTOMY DEVICES, AND IMAGING," filed Nov. 13, 2012; International Patent Application titled "ATHERECTOMY CATHETERS WITH IMAGING," filed herewith; and International Patent Application titled "BALLOON ATHERECTOMY CATHETERS WITH IMAGING," filed herewith, all of which are incorporated by reference in their entireties.

As shown in FIG. 5A, the distal end of the optical fiber 104 and the GRIN fiber 222 can sit away from the central axis 555 of an imaging catheter 502 such that the distal tip of the GRIN fiber 222 is near the outer edge 525 of the catheter 502 (i.e., where the diameter of the catheter is the largest). Further, in some embodiments, the catheter 502 can be configured to be placed in a blood vessel of 1-8 mm in diameter, e.g., 2-5 mm, such as approximately 3 mm in diameter. The catheter 502 can thus have a diameter of approximately 2 mm. By placing the GRIN fiber 222 off-axis and near the outer edge of the catheter 502, the focus can be located less than 1 mm from the outer edge 525 of the catheter 525, such as less than 0.8 mm or less than or equal to 0.7 mm from the outer edge 525 of the catheter 502, while still being located within the tissue of interest (e.g., the wall of the vessel). Thus, even after the light beam 203 bounces off of a reflective surface 180, such as a mirror or a prism, the maximum portion of the focal range lies inside the vessel structure, as indicated by the arrows 517. Having the maximum portion of the focal range lie inside the vessel structures improves both resolution and quality of the resulting image of the tissue.

Figure 6A:
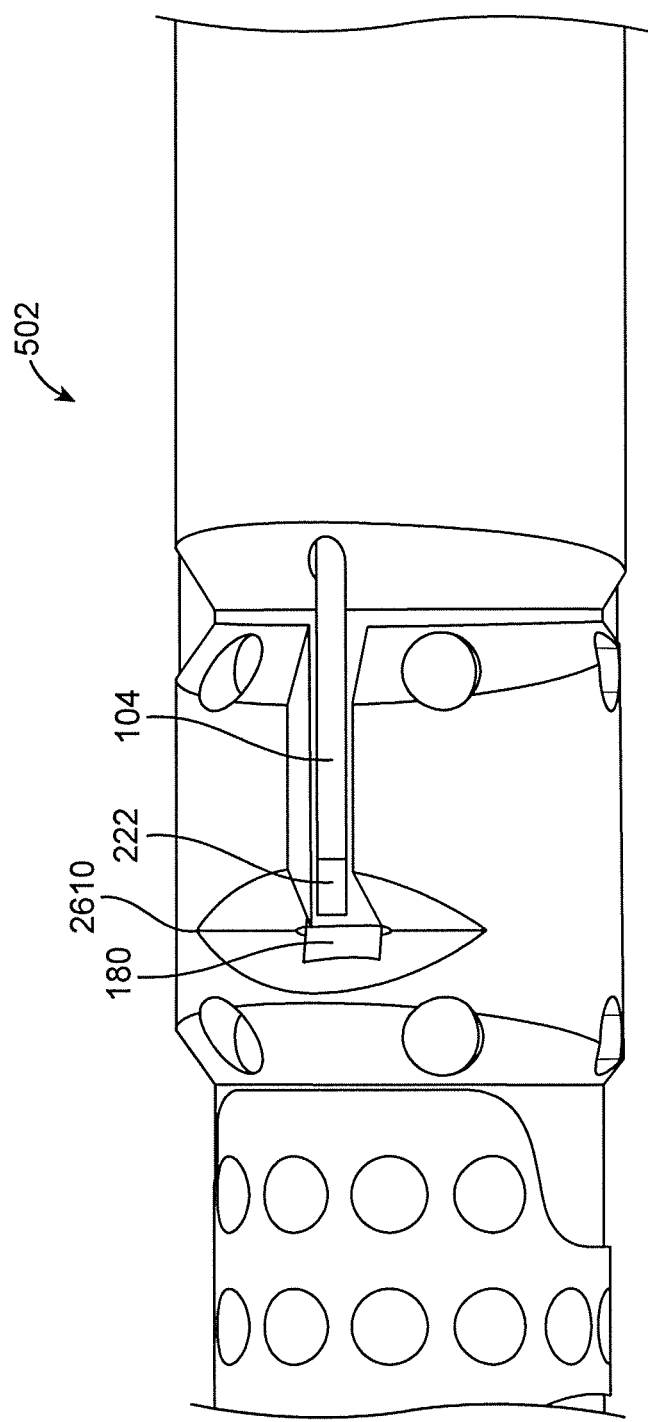
FIG. 6A is a top view of an exemplary mirror at the distal tip of an OCT catheter.
Figure 6B:
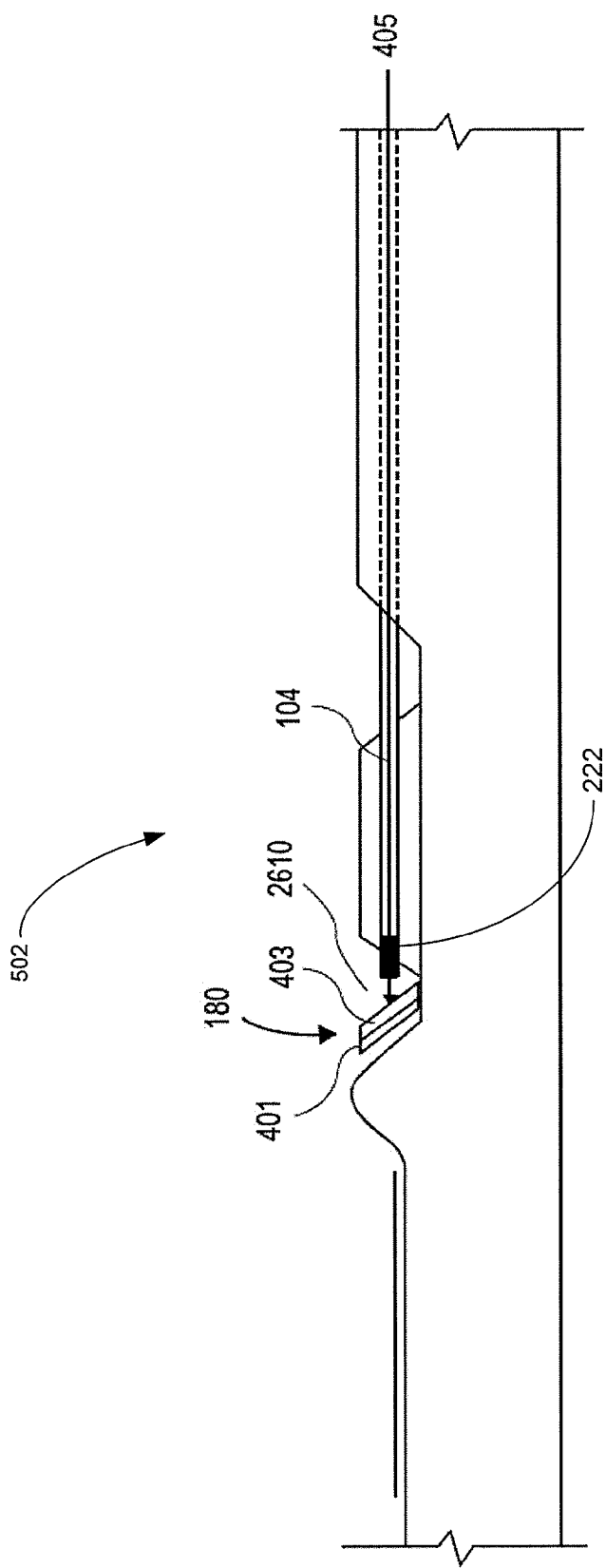
FIG. 6B is a cross-sectional side view the embodiment of FIG. 6A.

Referring to FIGS. 6A and 6B, the reflective surface 180 can be designed and optimized in a catheter 502 in order to fit into the small (approximately 2 mm) diameter of the catheter head and to reflect into a blood vessel tissue located up to 1-4 mm away from the side of the distal catheter tip. As shown in FIG. 6B, the catheter 502 can include a cut-out 2160 configured to hold the edge of the GRIN fiber 222 and the reflective surface 180, such as a mirror or a prism. In one embodiment, the reflective surface 180 can include a silicon die 401 having a reflective coating 403. The reflective coating 403 can be, for example, a gold coating. The reflective coating 403 can be greater than $\lambda_{min}/2\pi$ thick, where $\lambda_{min}$ is the wavelength of light in the optical fiber. For example, the metallic coating can be greater than about 2,800 Å thick.

Further, the surface of the silicon die 401 under the reflective coating 403 can be polished to less than 400 nm peak-to-peak roughness, such as better than 300 nm peak-to-peak roughness, for example about 200 nm peak-to-peak roughness. An adhesive, such as nickel, titanium, or chromium, can be used to adhere the gold coating to the silicon die. The adhesive can be between about 50 Å and 200 Å thick, such as about 100 Å thick. The reflective surface 180 of this configuration can be at least 95% reflective, such as 98% reflective.

The reflective surface 180 can be placed on a slope such that it is at an angle of between 30° and 60°, such as 45° with respect to a longitudinal axis 405 of the core of the optical fiber 104. Moreover, the reflective surface 180 can be configured such that the total distance that the light travels from the GRIN fiber 222 to the reflective surface 180 and out to the sample is between 100 and 400 μm, such as between 200 and 250 μm.

As shown in FIGS. 6A and 6B, an opening 2610 can be formed in the catheter 502, exposing the distal end of the GRIN fiber 222. The OCT reflective surface 180 can be placed in the opening near the distal tip of the catheter 104, and the interface medium can cover or embed the fiber 502 and opening 2610. Further, referring to FIG. 5B, the interface medium 106 can have an outer surface 539 (i.e. along the outer edge 525 of the catheter 502 closest to the target) that is concave, i.e., that forms a meniscus within the cut-out 2160. By having an outer surface 539 that is concave, the light beam 203 will hit the surface of the interface medium 106 at an angle (shown by the tangential line 215) such that any light that reflects back from the surface 539 will advantageous reflect at angles that are away from the distal end of the GRIN fiber 222. Having the majority of the reflected light stay away from the distal end of the GRIN fiber 222 advantageously ensures that the light does not couple back into the fiber 222/104 to form secondary reflection and subsequently create mirroring images on top of each other with an offset (sometimes termed "ghost images"). Because the GRIN fiber has a core diameter that is much larger than the core diameter of a traditional single mode optical fiber, the GRIN fiber has higher acceptance angle and thus is more prone to create secondary reflection. Accordingly, the concave surface 525 is especially advantageous when using a GRIN fiber 222.

Figure 7:
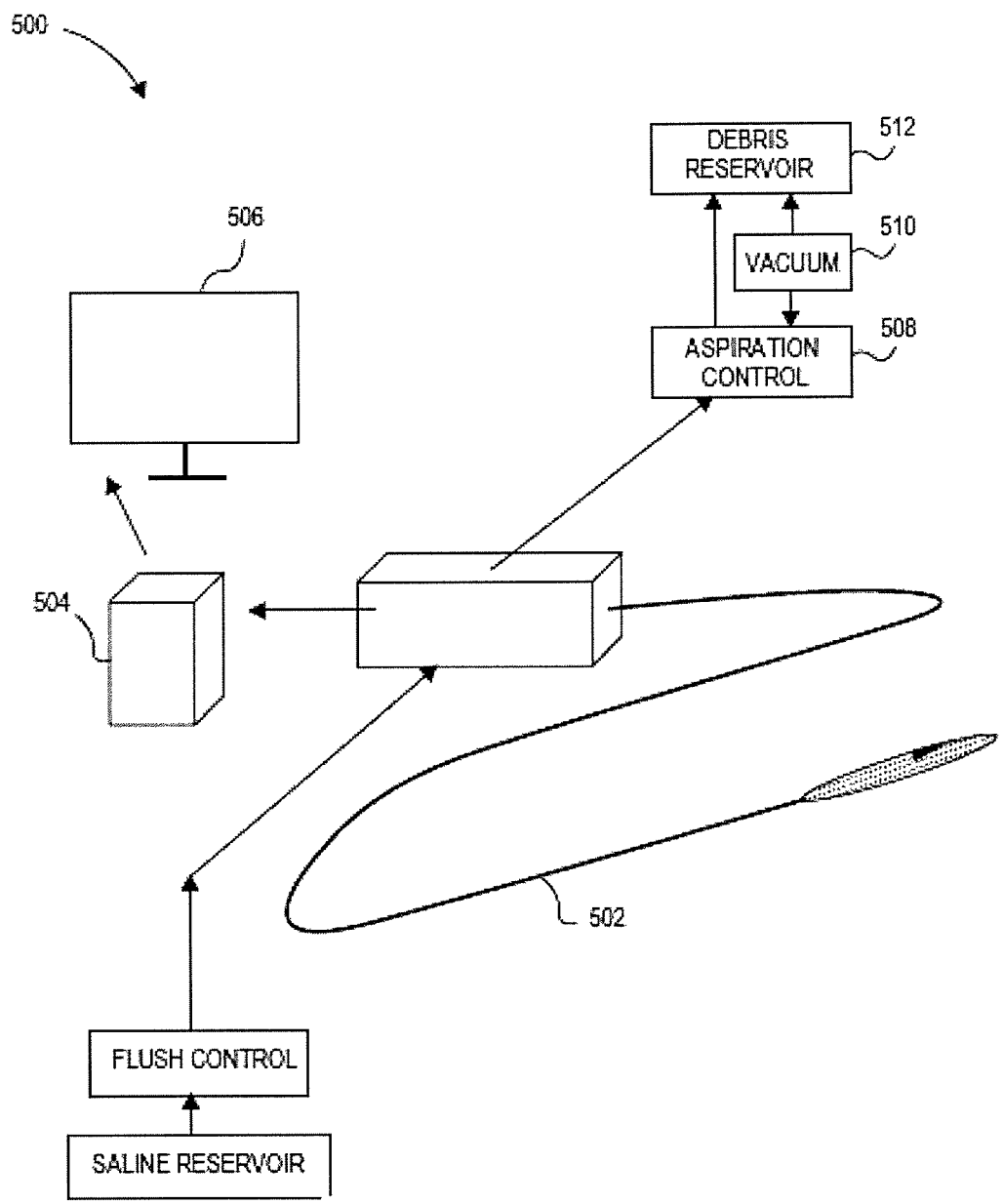
FIG. 7 shows a medical (intravascular) catheter system equipped with an OCT system.

FIG. 7 shows an overview of the main components of an OCT imaging system 500 including a fiber optic catheter 502. The catheter 502 can be sized to fit into a blood vessel, e.g. can be about 2 mm in diameter. In this configuration, the OCT optical apparatus 504 (including the light source, optical circulator, and detectors) can be located at the proximal end of the catheter 502, and can be connected to an image processor and a display 506. The distal end of the catheter 502 includes the image fiber and the mirror. The system 500 is designed to be used within the body of a patient for various medical purposes, such as occlusion crossing or atherectomy. Thus, other components, such as a vacuum 510, aspiration control 508, and a debris reservoir 512 may be useful.

The system described herein may be used to produce relatively narrow angle images of a portion of an interior lumen of a human body, such as the interior of a blood vessel. Looking at a section of a tissue through a single OCT optical fiber is limited in that the useful angle of view produced by a single OCT optical fiber is at most a few degrees. In order to produce a more medically useful panoramic view of a wide arc or swath from the interior of a blood vessel, such as 45°, 90°, 120°, or more, the catheter containing the optical fiber can be rotated.

The system described herein can produce images, e.g. images of tissue morphology, having an axial resolution of around 6-15 microns, e.g. 8-10 microns, and to depths of 1-2 mm depending on the optical properties of the sample being imaged. The axial resolution of the OCT system can be about ten times higher than that of a similar ultrasound system. The azimuthal resolution can be maintained to be less than 100 microns typically up to depths of 3-4 mm.

Figure 8:
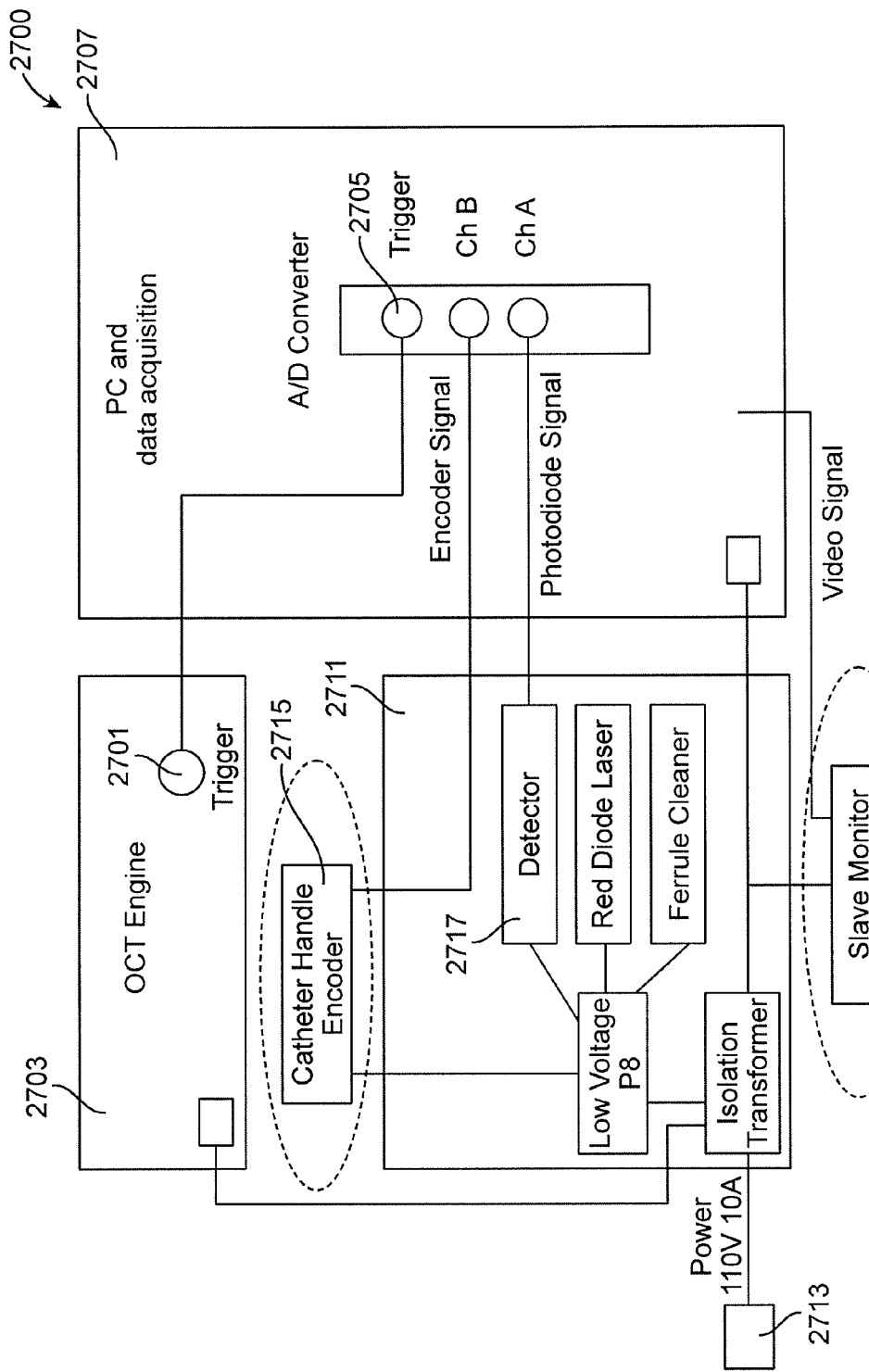
FIG. 8 shows a system for implementing the OCT system and catheter.

FIG. 8 shows a system 2700 for implementing the OCT system and catheter described herein. A power supply 2713 supplies power to the OCT engine 2703, the computer processor 2707, and the optical system 2711. A trigger 2701 in the OCT engine 2703 is connected to a trigger 2705 in the computer processor 2707 to begin processing of the image. Moreover, a catheter rotation encoder 2715 is attached to the computer processor 2707 to transfer signals related to the location and rotation of the optic fiber. The OCT detector 2717 is attached to the computer processor 2707 to process the final image. Finally, a video signal is sent from the computer processor 2707 to a monitor 2709 to output the image to the user.

In some embodiments, the OCT system and catheter described herein can image up to 1-2 mm in depth with axial resolutions around 8-10 microns, sufficient to give the physician highly detailed images almost to the cellular organization level and visibility beyond the maximum cut range of the catheter. Moreover, the OCT atherectomy catheter described in can advantageously have imaging capability with crossing-profile impact that is much smaller than traditional OCT systems and ultrasound transducers.

In one example, an image-guided interventional catheter (e.g., an OCT catheter as described above) may be used to address unmet needs in peripheral and coronary artery disease (atherosclerosis). The system may include a console having a modest footprint and in a cath lab without need for extensive integration into cath lab systems. In some variations, the systems described herein may be integrated with other catheter (e.g., guidance, control, imaging) systems. The system may be configured to allow a procedure to start/proceed/finish under fluoro guidance in the event of a system failure. The system is also configured to be compatible with sterile procedures.

As mentioned above, the OCT systems described herein may allow real-time information on intravascular lesion morphology and device orientation in the vessel. This and other features may also allow improved navigation precision around complex anatomy (e.g., bifurcations, ostials, tortuosity, cutting on a curve, etc.), and around stent struts. The catheters may be safely used to traverse diseased tissue while reducing incidence of perforations and dissections potentially associated with a more aggressive treatment strategy. The systems may also provide immediate assessment of acute procedural success, and a reduction in procedure time compared to contemporary interventional techniques. The systems described herein may allow imaging of vessel wall morphology in real time and at a level of precision that could assist the physician in making a "diseased/not-diseased" determination.

In one example, the OCT system is configured to allow tissue morphology to be imaged in real time with resolution routinely around 8-10 microns, and to depths of 1-2 mm depending on the optical properties of the tissue. The axial resolution of OCT is sufficiently high that the images presented to the operator substantially resemble histology from optical microscopy, and are as a result more intuitively interpreted than ultrasound or MRI/CT images. The depth to which OCT can image through tissue with minimal to moderate lipid content is sufficient to give the physician visibility beyond the maximum proposed depth of cut for an atherectomy catheter, allowing the safety margins of the putative cut to be assessed.

As mentioned, OCT has several other technical and economic advantages for catheter applications. The impact on catheter crossing profile of the OCT optical fiber is much smaller than for even the smallest comparable ultrasound transducer. The axial resolution of OCT is typically 10× higher than ultrasound; this translates directly to image interpretability. The limited depth of penetration of typical OCT devices is not of primary concern in this application in many applications, because it is known from prior atherectomy procedures that substantial clinical benefit can be obtained by removing several hundred micron thicknesses of tissue. The depth of penetration may be matched to the expected maximum cut depth. Regions of particularly deep or thick tissue (target tissue to be removed) may be identified and treated serially or separately. For example, highly lipid-rich tissues (necrotic cores) appear as dark voids in OCT images, typically with bright caps.

The center wavelength for the optical system may be chosen to provide sufficient depth of penetration, as well as compatibility with the components of the system. For example, the OCT systems may use light that can be transmitted through fused silica fiber optics (where the primary investment in cost and quality has been made). The wavelength range to 250-2000 nm may be particularly useful. Single mode fibers can be readily obtained at any of these wavelength ranges, although wavelengths above 400 nm may be preferable. Below 250 nm air-guiding fibers can also be used. It may be easier to "see" through small annuli of either blood, saline or mixtures by restricting the scan range of the source to regions where hemoglobin and water do not strongly absorb light. This leads to the use of a "biological window" between about 800 nm and 1.4 microns.

The dominant mechanism restricting penetration depth in biological tissue when using ballistic optical scattering techniques is the photon scattering cross-section in the tissue. Higher scattering cross-sections causes fewer photons to traverse from source to target and back ballistically, that is with only one scattering event at the target leading to a reduction in useful signal. The scattering cross-section scales as an inverse power of wavelength over the 250-2000 nm range, transitioning from an exponent of −4 at shorter wavelengths to a smaller value at longer wavelengths. The value decreases monotonically going from short to longer wavelengths. Therefore, if it is desired to see deeper in tissue, the wavelength range of the source should be biased to longer wavelengths. Moving to longer wavelengths may, in some embodiments, require a more sophisticated laser source to achieve the same resolution compared to imaging at shorter wavelengths, however this is a soluble technical problem.

In some variations, the system takes advantage of the widespread availability of cheap, high quality parts. For example, fiber-based telecommunications has evolved at three specific center wavelength ranges; 800 (LAN only), 1310 (O-band) and 1550 nm (C-band). The systems described herein may use a center wavelength to 1310 nm, though this does not mean that the other two wavelength ranges could not be made to work. For example, the 800 nm center wavelength range is routinely used in ophthalmology, where depth of penetration can be sacrificed for tissue layer resolution and where fiber delivery is not a requirement (free-space optics may be used). In some variations, the system works in the telecommunications O-band. In practice the range of center wavelength is 1315-1340 nm may be dictated by the availability of suitable laser sources in the O-band.

There are three primary categories of source/detector combinations in OCT, namely Time-Domain, Spectral-Domain (Fourier Domain or Spectral Radar) and Swept Source OCT. The examples of OCT systems described herein are swept source OCT (SS-OCT), which allow for video-rate imaging, few or no moving parts, a simple optical system suitable for fiber implementation, imaging to depths greater than 1 mm, and insensitivity to the rigors of a mobile environment.

As discussed above, several interferometer configurations may be used. The systems described herein are Common Path Interferometry (CPI) systems. This has several advantages given the goal of catheter based imaging with cost-constrained capital equipment and disposable devices. The SS-OCT with CPI system described herein preserves the Fellgett Advantage. Fellgett's advantage or the multiplex advantage is an improvement in spectroscopic techniques that is gained when an interferometer is used instead of a monochromator or scanning delay line. The improvement arises because when an interferometer is employed, the radiation that would otherwise be partially or wholly rejected by the monochromator or scanning delay line in its path retains its original intensity. This results in greater efficiency. This embodiment contrasts with the other systems, in which only a small fraction of the laser power is useful at any given time. For example, the Lightlab™ M2 system uses TD-OCT with a scanning delay line, which is equivalent for the purposes of the Fellgett Advantage to a monochromator. Clinically, the Fellgett advantage impacts imaging speed (frame update rate), allowing significant improvements in video display rates which translate to a reduction in ambiguity in interpreting the image.

The CPI systems described herein also preserve the Jacquinot Advantage. The Jacquinot advantage states that in a lossless optical system, the brightness of the object equals the brightness of the image. Assuming that losses due the optical components are negligible, an interferometer's output will be nearly equal in intensity to the input intensity, thus making it easier to detect the signal. This translates directly to image quality, and a more interpretable image.

The CPI system as described herein therefore makes highly efficient use of the laser power. Light is either used for the reference reflection or impinges on the tissue and is used to create signal. No light is lost in attenuators or additional optical components or unused reciprocal paths. This efficient use of laser power is most apparent in the ability of the system to display clinically relevant images of the intravascular environment in real time, without the need for extensive post processing or even on-the-fly image correction.

Furthermore, these systems are "down-lead insensitive", allowing the connection from catheter to console to be of almost arbitrary length without requiring a matched reference delay line to be shipped with each catheter. This minimizes the additional cost impact of the imaging components added to the catheter. It also allows a console component to be positioned almost anywhere, minimizing the potential disruption to work flow and minimizing the threat to a sterile field.

The systems described herein also minimize the number of optical components in the imaging system which could contribute to chromatic aberration. This minimization preserves the spectral fidelity of the laser source optimizing the layer resolution. This translates directly to image quality, and a more interpretable image.

The common-path systems described herein also have exceptional phase stability. Path length changes affecting the sample arm (temperature changes, stress-induced birefringence etc) also affect the reference arm identically. The distance from the ZPD (zero-pathlength difference) point (the reference plane) to the sample is physically fixed and is not subject to variability due to turbulence. This exceptional phase stability coupled with the exceptional phase stability of the OCT engine means that the Z-axis of the display (depth) has minimal jitter, in turn maximizing the real-time interpretability of the image. It also allows mathematical manipulation of the data that would otherwise be impossible. For example, one advantage of the systems described herein is the ability to perform pre-FFT averaging, which lowers the overall noise floor of the system again translating directly to image quality and interpretability.

In one example, the catheter is around 2 mm in diameter (7F compatible). In a saline-filled lumen, the system will be able to detect an interface (e.g., vessel wall) at 2 mm from the OD of the catheter. In this variation, the following parameters may be used for the catheter and system:

| Specifications | Value |
|---|---|
| Optimized Detector Bandwidth | DC - 10 MHz |
| Nyquist/Shannon rate | 20 MHz |
| Minimum number of points to sample for full resolution | 630 |

The detector may detect optical modulation on the carrier wave from DC to at least 10 MHz with no roll-off in sensitivity. To prevent aliasing (which complicates image interpretation) we may digitize the detector output at a minimum of 20 M-Samples/sec (Nyquist limit) to preserve interpretable real time imaging capability. We may thus capture at least 630 points per laser pulse at this digitizer rate to avoid undersampling the available laser bandwidth.

A practical resolution target is the intima of healthy coronary artery. The system resolution is capable of showing the intima (endothelial layer+internal elastic lamina) as a single sharp bright line on the display.

The system may have an impulse response of 8-10 microns. This resolution dictates the laser scan range requirements and the bandwidth requirements of all the optical components in the fiber harness through the equation:

$$\partial z = \frac{2\ln 2}{\pi} \frac{\lambda_0^2}{n\Delta\lambda}$$

Where $\delta z$ is the axial resolution, $\lambda$ is the wavelength, $\Delta\lambda$ is the wavelength range over which the laser scans, n is the refractive index of the medium and the other symbols have their usual meaning. The origin of this relationship is the Heisenberg Uncertainty Principle. Several observations accrue from this equation.

If the laser scan range $\Delta\lambda$ is not broad enough, $\delta z$ (the resolution) is compromised and an image of a step refractive index discontinuity will be blurred out over many pixels. If any of the optical components in the system restrict (alternatively called clipping or vignetting) the effective bandwidth of the system is reduced and the resolution may suffer. Since the resolution equation has the center wavelength squared in the numerator, as we move to longer center wavelengths for the reasons described above, commensurately larger laser scan range may achieve equivalent axial resolution. Ophthalmology is routinely performed at 800 or 1000 nm center wavelength where there is no need to image deeply into the retina, but where the available lasers allow extremely high resolution of the layers of the retina (down to 1-2 microns thickness).

In some variations, the OCT system has a scan range of >100 nm. The theoretical resolution of this engine is 6.35 microns in a medium with a refractive index of 1.35. Stipulating that we digitize at least at the Nyquist limit, fully sample the scanned bandwidth, and that the resealing procedure in the software does not distort the data, the theoretical resolution of this system is sufficient to show the intima of a healthy coronary artery at the impulse response limit.

The choice of 1310 nm as a center wavelength for the laser means that we may use standard commercial off-the-shelf telecommunications components which have guaranteed performance at this wavelength and for which standardized test protocols exist. Reasonable and customary incoming inspection procedures can be used to verify that the components going into the system will not deteriorate image quality.

As mentioned above, the system may include receiving electronics including a detector. Assuming that the operating center wavelength is 1315-1340 nm with a full-width half maximum responsivity of >100 nm, and that the detector operates as close as reasonably possible to the shot-noise limited regime, the system may have sufficient trans-impedance gain from the detector to allow the A/D card to operate at an input range where digitizer noise is not a dominant contributor to the noise floor of the system.

Manufacturing tolerances on the catheters will yield a range of distal tip reference reflection intensities. The detector may be configured or chosen so as not to saturate at the high manufacturing limit of the reference reflection power. In one example, the system uses a Fermionics FD80 photodiode in an FC receptacle package as the active element in the photodetector.

The system may also include a fiber harness designed to: 1) provide a low loss pathway from the laser to the catheter, 2) route signal light returning from the catheter to the detector, 3) allow the bleed-in of a red laser diode signal to allow rapid assessment of the integrity of the fiber from cable to distal tip, and 4) provide manufacturing, calibration and field service housekeeping signals to facilitate console production, validation and maintenance.

Figure 9:
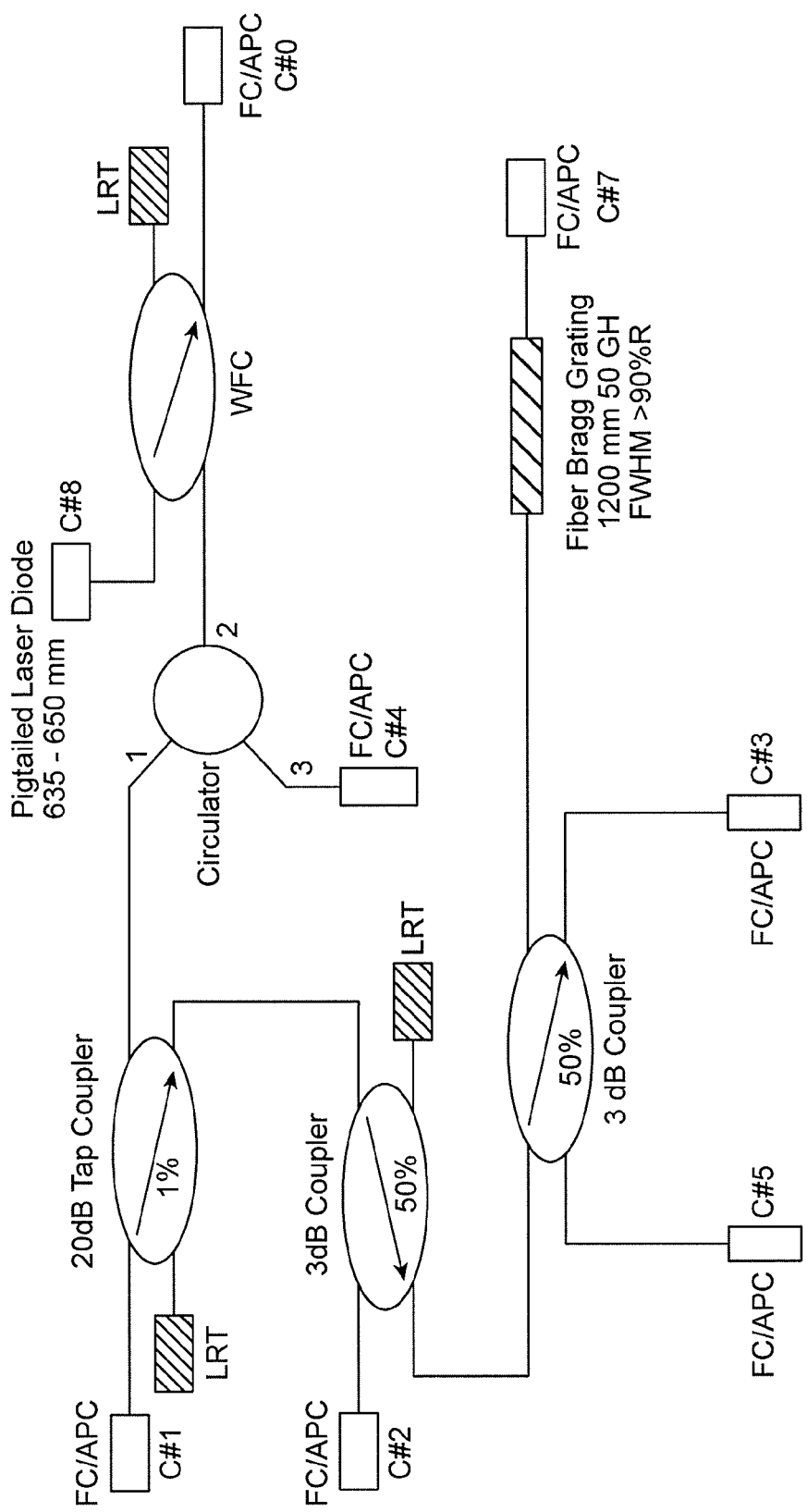
FIG. 9 shows one example of an optical circuit.

One primary component of the fiber harness may be a self-contained enclosure with bulkhead FC/APC receptacles on it and containing an optical circuit (such as the one shown in FIG. 9.

In one example, the fiber harness may be connected as: #1 Incoming OCT source (e.g., Santec) Santec output connected here. #2 Diagnostic port (OSA/Photodiode/MZI Calibration); #3 Diagnostic port (OSA/Photodiode/MZI Calibration); #4 Connection to Detector; #5 Reflected FBG Marker (Time/Wavelength Calibration Point); #6 Connection to Catheter; #7 Transmitted FBG Signal (Photodiode scope trigger); #8 Connection to red laser source. Connections may be made with single mode fiber with a cut-off of <1260 nm. The inputs/outputs do not need to be optically isolated.

In some variations, an electrical harness may be used. The electrical harness may be configured to: 1) provide isolation for the various electrical components in the imaging system; 2) distribute 110V to the OCT engine, slave monitor and computer; 3) provide regulated isolated housekeeping power at appropriate voltages and amperages to the detector, red diode laser, catheter handle azimuthal position encoder; 4) send the video signal to the remote monitor; and 5) receive the catheter handle azimuthal angle encoder signal back to the console.

Line power may enter the console through a standard IEC60320 type C14 male power cord entry connector. The power cord used may be Hospital Grade and may have a standard IEC60320 type C13 female connector at the console end. An isolation transformer can distribute LINE power to the OCT engine, slave monitor and computer through IEC standard power cords.

Figure 10:
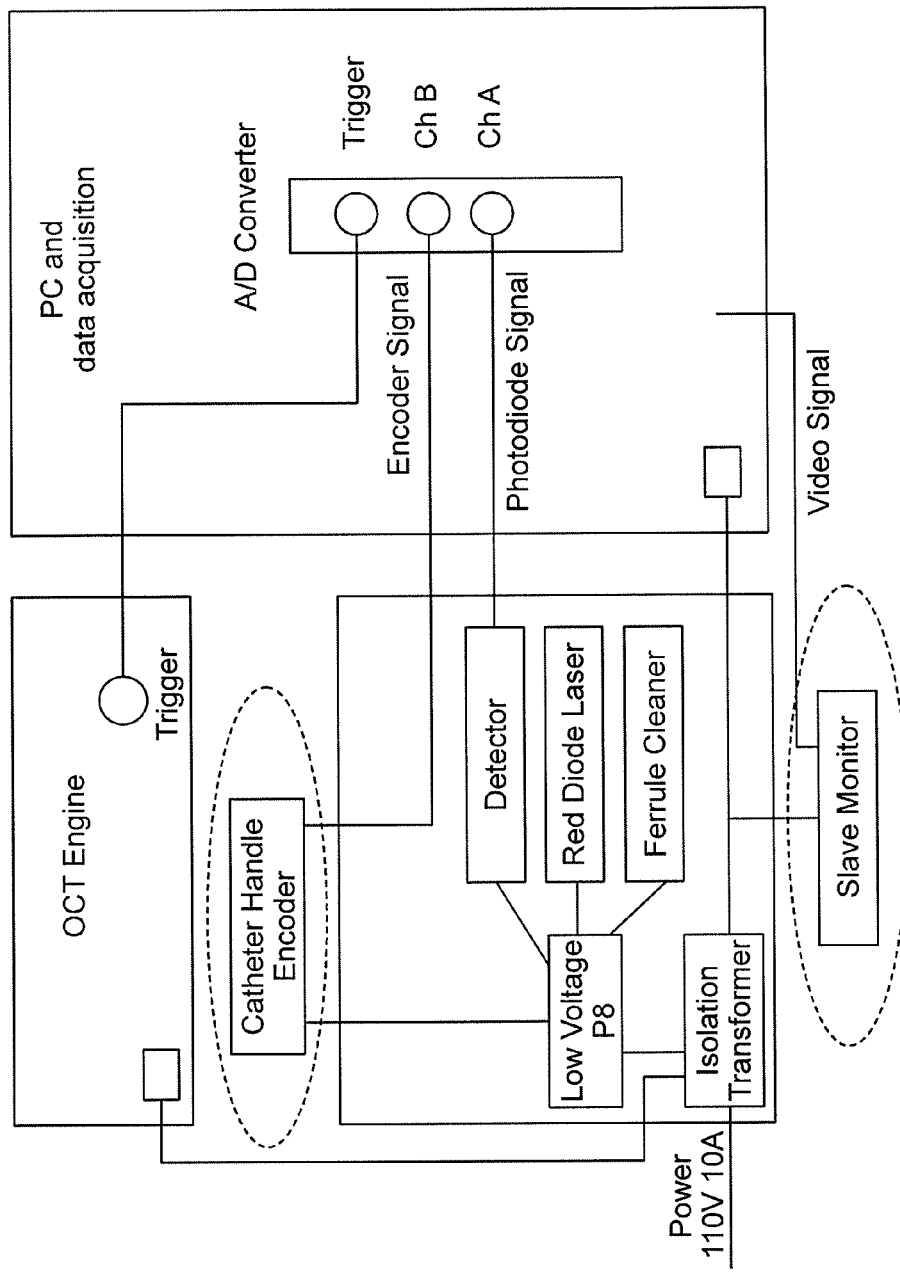
FIG. 10 is a schematic of an OCT system as described herein.

FIG. 10 shows one example of a schematic of an OCT system as described herein. In this example, items with dotted perimeters are outside the main console chassis enclosure. Analog signal interconnects are to be made with RG58 (U, A/U) patch cables terminated with BNC connectors. The (Santec) Trigger Out signal is a falling edge signal (high Z) and should not be terminated in 50 ohms. The Encoder Signal can be terminated with a MiniCircuits low pass filter module at the A/D card to remove high frequency spurious noise. The Detector Signal can be terminated with a MiniCircuits low pass filter module at the A/D card to remove any noise in an irrelevant frequency range.

The optical fiber may have a cut-off less than 1260 nm and have single mode performance between 1270 and 1380 nm (and be manufactured compatible with SMF-28 standards). The mechanical connections (pigtail and patch cable) may include a simplex cable, and an inner loose tube Teflon Aramid fiber inner annulus to prevent stretching. The outer Jacket may be 2 mm polyurethane. The connector may be a Diamond E2108.6 connector with a 0.25 dB maximum insertion loss and a −65 dB maximum return loss.

The distal tip reference reflection (mirror) may include at least one (1) reflective interface, and may have a return loss of −33.5 dB (Nominal (31-35 dB)). There may be 200-250 microns solid transparent offset from interface to minimum tissue approach point. Interceding optical discontinuities between console and catheter distal tip may be kept to less than 65 dB return loss maximum for any individual surface. The number of reflective interfaces separated by less than 8 mm may be minimized. The parameters above are exemplary only, and may be varied as understood by those of skill in the art, while still remaining in the spirit of the invention as described herein.

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A system for optical coherence tomography, comprising:
   a source of optical radiation;
   an optical fiber;
   a graded index fiber attached to a distal end of the optical fiber, wherein the optical fiber and the graded index fiber are together configured to provide a common path for optical radiation reflected from a reference interface at a distal end of the graded index fiber and from a target;
   receiving electronics configured to receive the optical radiation reflected from the reference interface and the target; and
   a processor to generate an image of the target based upon the optical radiation received by the receiving electronics.

2. The system of claim 1, wherein a secondary reflection of optical radiation from an interface between the optical fiber and the graded index fiber is less than −60 dB.

3. The system of claim 1, wherein the reference interface provides a reference reflection of between −28 and −42 dB.

4. The system of claim 1, further comprising an interface medium at the reference interface and in optical contact with the graded index fiber.

5. The system of claim 4, wherein a refractive index of the graded index fiber and a refractive index of the reference medium are mismatched such that the receiving electronics operate in a total noise range that is within 5 dB of the shot noise limit.

6. The system of claim 4, wherein the reference interface is angled with respect to a longitudinal axis of the graded index fiber such the receiving electronics operate in a total noise range that is within 5 dB of the shot noise limit.

7. The system of claim 4, wherein a surface of the interface medium that is closest to the target is concave.

8. The system of claim 4, wherein the interface medium is an adhesive.

9. The system of claim 1, wherein an outer diameter of the graded index fiber and a protective coating around the graded index fiber is less than 0.01 inches.

10. A system for optical coherence tomography, comprising:
    a source of optical radiation;
    an optical fiber;
    a graded index fiber attached to a distal end of the optical fiber, wherein the optical fiber and the graded index fiber are together configured to provide a common path for optical radiation reflected from a reference interface at a distal end of the graded index fiber and from a target;
    receiving electronics configured to receive the optical radiation reflected from the reference interface and the target; and
    a processor to generate an image of the target based upon the optical radiation received by the receiving electronics;
    wherein a secondary reflection of optical radiation from an interface between the optical fiber and the graded index fiber is less than −60 dB.

11. The system of claim 10, wherein the reference interface provides a reference reflection of between −28 and −42 dB.

12. The system of claim 10, further comprising an interface medium at the reference interface and in optical contact with the graded index fiber.

13. The system of claim 12, wherein a refractive index of the graded index fiber and a refractive index of the reference medium are mismatched such that the receiving electronics operate in a total noise range that is within 5 dB of the shot noise limit.

14. The system of claim 12, wherein the reference interface is angled with respect to a longitudinal axis of the graded index fiber such the receiving electronics operate in a total noise range that is within 5 dB of the shot noise limit.

15. The system of claim 12, wherein a surface of the interface medium that is closest to the target is concave.

16. The system of claim 12, wherein the interface medium is an adhesive.

17. The system of claim 10, wherein an outer diameter of the graded index fiber and a protective coating around the graded index fiber is less than 0.01 inches.

* * * * *